(12) United States Patent
Shohat

(10) Patent No.: US 11,033,398 B2
(45) Date of Patent: Jun. 15, 2021

(54) SHOULDER IMPLANT FOR SIMULATING A BURSA

(71) Applicant: Ortho-Space Ltd., Caesarea (IL)

(72) Inventor: Shaul Shohat, Kfar HaOranim (IL)

(73) Assignee: Ortho-Space Ltd.

( * ) Notice: Subject to any disclaimer, the term of this patent is extended or adjusted under 35 U.S.C. 154(b) by 458 days.

(21) Appl. No.: 14/305,311

(22) Filed: Jun. 16, 2014

(65) Prior Publication Data

US 2014/0296987 A1     Oct. 2, 2014

Related U.S. Application Data

(63) Continuation of application No. 12/531,332, filed as application No. PCT/IL2008/000347 on Mar. 13, 2008, now Pat. No. 8,753,390.
(Continued)

(51) Int. Cl.
*A61F 2/40*     (2006.01)
*A61B 17/70*    (2006.01)
(Continued)

(52) U.S. Cl.
CPC ............. *A61F 2/40* (2013.01); *A61B 17/562* (2013.01); *A61B 17/7061* (2013.01);
(Continued)

(58) Field of Classification Search
USPC ........................................... 623/14.11, 11.11
See application file for complete search history.

(56) References Cited

U.S. PATENT DOCUMENTS

| 3,384,113 A | 5/1968 | Pennisi |
| 3,631,854 A | 1/1972 | Fryer |

(Continued)

FOREIGN PATENT DOCUMENTS

| CN | 2203592 | 7/1995 |
| CN | 1408451 | 4/2003 |

(Continued)

OTHER PUBLICATIONS

Official Copy of Decision of Rejection dated Oct. 7, 2014 From the Japanese Patent Office Re. Application No. 2013-99793 and Its Translation Into English.
(Continued)

*Primary Examiner* — Jerrah Edwards
*Assistant Examiner* — Christine L Nelson
(74) *Attorney, Agent, or Firm* — Lerner, David, Littenberg, Krumholz & Mentlik, LLP

(57) ABSTRACT

A shoulder implant for simulating a naturally occurring bursa proximal to or in lieu of a subacromial bursa, the shoulder implant comprising: an expandable member expandable to a size and/or a shape sufficient to fill a space beneath an acromion and/or a coracoid process of the shoulder, the space defines a filled volume less than a maximal volume occupied by the expandable member if fully expanded; and an amount of filler for filling the expandable member to the filled volume, such that, when implanted, the expandable member is configured to cushion and facilitate motion between a tendon and/or ligament of a rotator cuff, and a bone part in the shoulder.

25 Claims, 11 Drawing Sheets

Related U.S. Application Data

(60) Provisional application No. 60/918,051, filed on Mar. 15, 2007.

(51) Int. Cl.
    *A61B 17/56*         (2006.01)
    *A61B 17/72*         (2006.01)
    *A61B 17/88*         (2006.01)
    *A61B 17/00*         (2006.01)

(52) U.S. Cl.
CPC ...... *A61B 17/7097* (2013.01); *A61B 17/7275* (2013.01); *A61B 17/8855* (2013.01); *A61B 17/8805* (2013.01); *A61B 2017/00557* (2013.01); *A61F 2250/0003* (2013.01)

(56) References Cited

U.S. PATENT DOCUMENTS

| | | |
|---|---|---|
| 3,701,771 A | 10/1972 | Almen et al. |
| 3,800,788 A | 4/1974 | White |
| 3,875,595 A | 4/1975 | Froning |
| 4,364,392 A | 12/1982 | Strother et al. |
| 4,364,921 A | 12/1982 | Speck et al. |
| 4,513,058 A | 4/1985 | Martin |
| 4,638,803 A | 1/1987 | Rand |
| 4,662,883 A | 5/1987 | Bell et al. |
| 4,669,478 A | 6/1987 | Robertson |
| 4,719,918 A | 1/1988 | Bonomo et al. |
| 4,798,205 A | 1/1989 | Bonomo et al. |
| 4,819,637 A | 4/1989 | Dormandy, Jr. et al. |
| 4,892,550 A | 1/1990 | Huebsch |
| 4,906,244 A | 3/1990 | Pinchuk et al. |
| 4,932,938 A | 6/1990 | Goldberg et al. |
| 4,932,956 A | 6/1990 | Reddy et al. |
| 4,932,958 A | 6/1990 | Reddy et al. |
| 5,002,556 A | 3/1991 | Ishida et al. |
| 5,021,043 A | 6/1991 | Becker et al. |
| 5,033,481 A | 7/1991 | Heyler, III |
| 5,046,489 A | 9/1991 | Gibson |
| 5,071,410 A | 12/1991 | Pazell |
| 5,071,429 A | 12/1991 | Pinchuk et al. |
| 5,102,413 A | 4/1992 | Poddar |
| 5,122,113 A | 6/1992 | Hattler |
| 5,163,949 A | 11/1992 | Bonutti |
| 5,163,950 A | 11/1992 | Pinchuk et al. |
| 5,176,692 A | 1/1993 | Wilk et al. |
| 5,176,698 A | 1/1993 | Burns et al. |
| 5,181,921 A | 1/1993 | Makita et al. |
| 5,222,970 A | 6/1993 | Reeves |
| 5,282,785 A | 2/1994 | Shapland et al. |
| 5,286,254 A | 2/1994 | Shapland et al. |
| 5,295,994 A | 3/1994 | Bonutti |
| 5,318,586 A | 6/1994 | Ereren et al. |
| 5,331,975 A | 7/1994 | Bonutti |
| 5,334,210 A | 8/1994 | Gianturco et al. |
| 5,336,252 A | 8/1994 | Cohen |
| 5,344,451 A | 9/1994 | Dayton |
| 5,344,459 A | 9/1994 | Swartz |
| 5,370,691 A | 12/1994 | Samson |
| 5,423,850 A | 6/1995 | Berger |
| 5,425,357 A | 6/1995 | Moll et al. |
| 5,458,612 A | 10/1995 | Chin |
| 5,468,245 A | 11/1995 | Vargas, III |
| 5,480,400 A | 1/1996 | Berger |
| 5,496,203 A * | 3/1996 | Murray ............... A63H 27/10 446/221 |
| 5,507,770 A | 4/1996 | Turk |
| 5,507,808 A * | 4/1996 | Becker ............... A61F 2/12 251/349 |
| 5,514,143 A | 5/1996 | Bonutti |
| 5,514,153 A | 5/1996 | Bonutti |
| 5,516,522 A | 5/1996 | Peyman et al. |
| 5,524,633 A | 6/1996 | Heaven et al. |
| 5,547,472 A | 8/1996 | Onishi et al. |
| 5,549,625 A | 8/1996 | Bircoll |
| 5,571,179 A | 11/1996 | Manders et al. |
| 5,571,189 A | 11/1996 | Kuslich |
| 5,575,759 A | 11/1996 | Moll et al. |
| 5,632,762 A | 5/1997 | Myler |
| 5,641,505 A | 6/1997 | Bowald et al. |
| 5,645,560 A | 7/1997 | Crocker et al. |
| 5,653,758 A | 8/1997 | Daniels et al. |
| 5,658,310 A | 8/1997 | Berger |
| 5,658,324 A | 8/1997 | Bailey, Sr. et al. |
| 5,658,329 A | 8/1997 | Purkait |
| 5,662,712 A | 9/1997 | Pathak et al. |
| 5,667,520 A | 9/1997 | Bonutti |
| 5,674,295 A | 10/1997 | Ray et al. |
| 5,683,405 A | 11/1997 | Yacoubian et al. |
| 5,704,893 A | 1/1998 | Timm |
| 5,720,762 A | 2/1998 | Bass |
| 5,725,568 A | 3/1998 | Hastings |
| 5,746,762 A | 5/1998 | Bass |
| 5,746,763 A | 5/1998 | Benderev et al. |
| 5,769,884 A | 6/1998 | Solovay |
| 5,776,159 A | 7/1998 | Young |
| 5,779,672 A | 7/1998 | Dormandy, Jr. |
| 5,779,728 A | 7/1998 | Lunsford et al. |
| 5,798,096 A | 8/1998 | Pavlyk |
| 5,823,995 A | 10/1998 | Fitzmaurice et al. |
| 5,827,289 A | 10/1998 | Reiley et al. |
| 5,827,318 A | 10/1998 | Bonutti |
| 5,843,116 A | 12/1998 | Crocker et al. |
| 5,860,997 A | 1/1999 | Bonutti |
| 5,871,537 A | 2/1999 | Holman et al. |
| 5,888,196 A | 3/1999 | Bonutti |
| 5,925,058 A | 7/1999 | Smith et al. |
| 5,935,667 A | 8/1999 | Calcote et al. |
| 5,941,909 A | 8/1999 | Purkait |
| 5,954,739 A | 9/1999 | Bonutti |
| 5,968,068 A | 10/1999 | Dehdashtian et al. |
| 5,971,992 A | 10/1999 | Solar |
| 5,972,015 A | 10/1999 | Scribner et al. |
| 5,979,452 A | 11/1999 | Fogarty et al. |
| 5,984,942 A | 11/1999 | Alden et al. |
| 6,017,305 A | 1/2000 | Bonutti |
| 6,018,094 A | 1/2000 | Fox |
| 6,019,781 A | 2/2000 | Worland |
| 6,027,486 A | 2/2000 | Crocker et al. |
| 6,027,517 A | 2/2000 | Crocker et al. |
| 6,036,640 A | 3/2000 | Corace et al. |
| 6,042,596 A | 3/2000 | Bonutti |
| 6,066,154 A | 5/2000 | Reiley et al. |
| 6,068,626 A | 5/2000 | Harrington et al. |
| 6,074,341 A | 6/2000 | Anderson et al. |
| 6,099,547 A | 8/2000 | Gellman et al. |
| 6,102,928 A | 8/2000 | Bonutti |
| 6,106,541 A | 8/2000 | Hurbis |
| 6,117,165 A | 9/2000 | Becker |
| 6,120,523 A | 9/2000 | Crocker et al. |
| 6,171,236 B1 | 1/2001 | Bonutti |
| 6,186,978 B1 | 2/2001 | Samson et al. |
| 6,187,023 B1 | 2/2001 | Bonutti |
| 6,214,045 B1 | 4/2001 | Corbitt et al. |
| 6,235,043 B1 | 5/2001 | Reiley et al. |
| 6,240,924 B1 | 6/2001 | Fogarty et al. |
| 6,248,110 B1 | 6/2001 | Reiley et al. |
| 6,248,131 B1 | 6/2001 | Felt et al. |
| 6,280,456 B1 | 8/2001 | Scribner et al. |
| 6,280,457 B1 | 8/2001 | Wallace et al. |
| 6,293,960 B1 | 9/2001 | Ken |
| 6,306,081 B1 | 10/2001 | Ishikawa et al. |
| 6,306,177 B1 | 10/2001 | Felt et al. |
| 6,312,462 B1 | 11/2001 | McDermott et al. |
| 6,319,264 B1 | 11/2001 | Tormala et al. |
| 6,331,191 B1 | 12/2001 | Chobotov |
| 6,352,551 B1 | 3/2002 | Wang |
| 6,371,904 B1 | 4/2002 | Sirimanne et al. |
| 6,379,329 B1 | 4/2002 | Naglreiter et al. |
| 6,391,538 B1 | 5/2002 | Vyavahare et al. |
| 6,395,019 B2 | 5/2002 | Chobotov |
| 6,395,208 B1 | 5/2002 | Herweck et al. |
| 6,409,741 B1 | 6/2002 | Crocker et al. |

(56) References Cited

U.S. PATENT DOCUMENTS

| | | |
|---|---|---|
| 6,409,749 B1 | 6/2002 | Maynard |
| 6,419,701 B1 | 7/2002 | Cook et al. |
| 6,423,032 B2 | 7/2002 | Parodi |
| 6,423,083 B2 | 7/2002 | Reiley et al. |
| 6,443,941 B1 | 9/2002 | Slepian et al. |
| 6,451,042 B1 | 9/2002 | Bonutti |
| 6,500,190 B2 | 12/2002 | Greene, Jr. et al. |
| 6,503,265 B1 | 1/2003 | Fogarty et al. |
| 6,527,693 B2 | 3/2003 | Munro, III et al. |
| 6,530,878 B2 | 3/2003 | Silverman et al. |
| 6,533,799 B1 | 3/2003 | Bouchier |
| 6,547,767 B1 | 4/2003 | Moein |
| 6,591,838 B2 | 7/2003 | Durgin |
| 6,599,275 B1 | 7/2003 | Fischer, Jr. |
| 6,607,544 B1 | 8/2003 | Boucher et al. |
| 6,613,052 B1 | 9/2003 | Kinnett |
| 6,616,673 B1 | 9/2003 | Stone et al. |
| 6,620,181 B1 | 9/2003 | Bonutti |
| 6,623,505 B2 | 9/2003 | Scribner et al. |
| 6,632,235 B2 | 10/2003 | Weikel et al. |
| 6,638,308 B2 | 10/2003 | Corbitt et al. |
| 6,652,587 B2 | 11/2003 | Felt et al. |
| 6,663,647 B2 | 12/2003 | Reiley et al. |
| 6,668,836 B1 | 12/2003 | Greenburg et al. |
| 6,673,290 B1 | 1/2004 | Whayne et al. |
| 6,706,064 B1 | 3/2004 | Anson |
| 6,716,216 B1 | 4/2004 | Boucher et al. |
| 6,719,773 B1 | 4/2004 | Boucher et al. |
| 6,733,533 B1 | 5/2004 | Lozier |
| 6,746,465 B2 | 6/2004 | Diederich et al. |
| 6,755,862 B2 | 6/2004 | Keynan |
| 6,800,082 B2 | 10/2004 | Rousseau |
| 6,837,850 B2 | 1/2005 | Suddaby |
| 6,860,892 B1 | 3/2005 | Tanaka et al. |
| 6,872,215 B2 | 3/2005 | Crocker et al. |
| 6,881,226 B2 | 4/2005 | Corbitt et al. |
| 6,899,719 B2 | 5/2005 | Reiley et al. |
| 6,932,834 B2 | 8/2005 | Lizardi et al. |
| 6,958,212 B1 | 10/2005 | Hubbell et al. |
| 6,979,341 B2 | 12/2005 | Scribner et al. |
| 6,981,980 B2 | 1/2006 | Sampson et al. |
| 6,981,981 B2 | 1/2006 | Reiley et al. |
| 6,994,092 B2 | 2/2006 | van der Burg et al. |
| 7,001,431 B2 | 2/2006 | Bao et al. |
| 7,029,487 B2 | 4/2006 | Greene, Jr. et al. |
| 7,044,954 B2 | 5/2006 | Reiley et al. |
| 7,060,100 B2 | 6/2006 | Ferree et al. |
| 7,077,865 B2 | 7/2006 | Bao et al. |
| 7,144,398 B2 | 12/2006 | Chern Lin et al. |
| 7,156,860 B2 | 1/2007 | Wallsten |
| 7,156,861 B2 | 1/2007 | Scribner et al. |
| 7,160,325 B2 | 1/2007 | Morningstar |
| 7,166,121 B2 | 1/2007 | Reiley et al. |
| 7,201,762 B2 | 4/2007 | Greene, Jr. et al. |
| 7,217,273 B2 | 5/2007 | Bonutti |
| 7,226,481 B2 | 6/2007 | Kuslich |
| 7,241,303 B2 | 7/2007 | Reiss et al. |
| 7,261,720 B2 | 8/2007 | Stevens et al. |
| 7,320,709 B2 | 1/2008 | Felt et al. |
| 7,368,124 B2 | 5/2008 | Chun et al. |
| 7,404,791 B2 | 7/2008 | Linares et al. |
| 7,476,235 B2 | 1/2009 | Diederich et al. |
| 7,488,337 B2 | 2/2009 | Saab et al. |
| 7,491,236 B2 | 2/2009 | Cragg et al. |
| 7,524,274 B2 | 4/2009 | Patrick et al. |
| 7,544,213 B2 | 6/2009 | Adams |
| 7,583,520 B2 | 9/2009 | Aso |
| 7,589,980 B2 | 9/2009 | Aso |
| 7,601,113 B2 | 10/2009 | Lebovic et al. |
| 7,632,291 B2 | 12/2009 | Stephens et al. |
| 7,637,948 B2 | 12/2009 | Corbitt |
| 7,699,894 B2 | 4/2010 | O'Neil et al. |
| 7,713,301 B2 | 5/2010 | Bao et al. |
| 7,749,267 B2 | 7/2010 | Karmon |
| 7,766,965 B2 | 8/2010 | Bao et al. |
| 7,799,077 B2 | 9/2010 | Lang et al. |
| 7,819,881 B2 | 10/2010 | Stone et al. |
| 7,871,438 B2 | 1/2011 | Corbitt |
| 8,317,865 B2 | 11/2012 | Osorio et al. |
| 8,328,875 B2 | 12/2012 | Linares |
| 8,361,157 B2 | 1/2013 | Boutten et al. |
| 8,377,135 B1 | 2/2013 | McLeod et al. |
| 8,512,347 B2 | 8/2013 | McCormack et al. |
| 8,551,172 B2 | 10/2013 | Park |
| 8,556,971 B2 | 10/2013 | Lang |
| 8,632,601 B2 | 1/2014 | Howald et al. |
| 8,753,390 B2 | 6/2014 | Shohat |
| 8,771,363 B2 | 7/2014 | Grotz |
| 8,894,713 B2 | 11/2014 | Shohat et al. |
| 8,900,304 B1 | 12/2014 | Alobaid |
| 8,926,622 B2 | 1/2015 | McKay |
| 9,132,015 B2 | 9/2015 | Bromer |
| 9,271,779 B2 | 3/2016 | Bonutti |
| 9,289,307 B2 | 3/2016 | Shohat |
| 9,345,577 B2 | 5/2016 | Vanleeuwen et al. |
| 9,408,709 B2 | 8/2016 | Wirtel, III et al. |
| 9,533,024 B2 | 1/2017 | Sevrain et al. |
| 9,545,316 B2 | 1/2017 | Ashley et al. |
| 9,545,321 B2 | 1/2017 | Hibri et al. |
| 9,585,761 B2 | 3/2017 | Teisen et al. |
| 9,622,873 B2 | 4/2017 | McCormack |
| 9,687,353 B2 | 6/2017 | Afzal |
| 9,750,534 B2 | 9/2017 | Philippon et al. |
| 9,750,611 B2 | 9/2017 | Fell |
| 9,757,241 B2 | 9/2017 | Grotz |
| 9,770,337 B2 | 9/2017 | Shohat |
| 9,808,345 B2 | 11/2017 | Grotz |
| 9,949,838 B2 | 4/2018 | Vanleeuwen et al. |
| 10,004,605 B2 | 6/2018 | Grotz |
| 2001/0004710 A1 | 6/2001 | Felt et al. |
| 2001/0008976 A1 | 7/2001 | Wang |
| 2001/0011174 A1 | 8/2001 | Reiley et al. |
| 2001/0041936 A1 | 11/2001 | Corbitt et al. |
| 2001/0049531 A1 | 12/2001 | Reiley et al. |
| 2002/0010514 A1 | 1/2002 | Burg et al. |
| 2002/0013600 A1 | 1/2002 | Scribner et al. |
| 2002/0016626 A1 | 2/2002 | DiMatteo et al. |
| 2002/0045909 A1 | 4/2002 | Kimura et al. |
| 2002/0052653 A1 | 5/2002 | Durgin |
| 2002/0058947 A1 | 5/2002 | Hochschuler et al. |
| 2002/0082608 A1 | 6/2002 | Reiley et al. |
| 2002/0127264 A1 | 9/2002 | Felt et al. |
| 2002/0143402 A1 | 10/2002 | Steinberg |
| 2002/0147497 A1 | 10/2002 | Belef et al. |
| 2002/0156489 A1 | 10/2002 | Gellman et al. |
| 2002/0161388 A1 | 10/2002 | Samuels et al. |
| 2002/0165570 A1 | 11/2002 | Mollenauer et al. |
| 2002/0173852 A1 | 11/2002 | Felt et al. |
| 2002/0177866 A1 | 11/2002 | Weikel et al. |
| 2002/0183778 A1 | 12/2002 | Reiley et al. |
| 2002/0183850 A1 | 12/2002 | Felt et al. |
| 2003/0018352 A1 | 1/2003 | Mollenauer et al. |
| 2003/0018388 A1 | 1/2003 | Comer |
| 2003/0023260 A1 | 1/2003 | Bonutti |
| 2003/0028196 A1* | 2/2003 | Bonutti ............... A61B 17/025 606/87 |
| 2003/0028211 A1 | 2/2003 | Crocker et al. |
| 2003/0032963 A1 | 2/2003 | Reiss et al. |
| 2003/0033017 A1 | 2/2003 | Lotz et al. |
| 2003/0036728 A1 | 2/2003 | Samson et al. |
| 2003/0036797 A1 | 2/2003 | Malaviya et al. |
| 2003/0040800 A1 | 2/2003 | Li et al. |
| 2003/0074084 A1 | 4/2003 | Nakao |
| 2003/0078602 A1 | 4/2003 | Rousseau |
| 2003/0093107 A1 | 5/2003 | Parsonage et al. |
| 2003/0105469 A1 | 6/2003 | Karmon |
| 2003/0114878 A1 | 6/2003 | Diederich et al. |
| 2003/0114934 A1 | 6/2003 | Steinberg |
| 2003/0130664 A1 | 7/2003 | Boucher et al. |
| 2003/0147935 A1 | 8/2003 | Binette et al. |
| 2003/0181800 A1 | 9/2003 | Bonutti |
| 2003/0181939 A1 | 9/2003 | Bonutti |
| 2003/0191489 A1 | 10/2003 | Reiley et al. |
| 2003/0195547 A1 | 10/2003 | Scribner et al. |

(56) References Cited

U.S. PATENT DOCUMENTS

| | | |
|---|---|---|
| 2003/0195628 A1 | 10/2003 | Bao et al. |
| 2003/0212426 A1 | 11/2003 | Olson et al. |
| 2003/0216776 A1 | 11/2003 | Mollenauer et al. |
| 2003/0220648 A1 | 11/2003 | Osorio et al. |
| 2003/0220649 A1 | 11/2003 | Bao et al. |
| 2003/0229372 A1 | 12/2003 | Reiley et al. |
| 2003/0236513 A1 | 12/2003 | Schwarz et al. |
| 2004/0010263 A1 | 1/2004 | Boucher et al. |
| 2004/0038874 A1 | 2/2004 | Omoigui |
| 2004/0049269 A1 | 3/2004 | Corbin et al. |
| 2004/0073107 A1 | 4/2004 | Sioshansi et al. |
| 2004/0083002 A1 | 4/2004 | Belef et al. |
| 2004/0093004 A1 | 5/2004 | Schultz |
| 2004/0093008 A1 | 5/2004 | Zamore |
| 2004/0097794 A1 | 5/2004 | Bonutti |
| 2004/0097949 A1 | 5/2004 | Bonutti |
| 2004/0098015 A1 | 5/2004 | Weikel et al. |
| 2004/0098016 A1 | 5/2004 | Bonutti |
| 2004/0098017 A1 | 5/2004 | Saab et al. |
| 2004/0107000 A1 | 6/2004 | Felt et al. |
| 2004/0117019 A1 | 6/2004 | Trieu et al. |
| 2004/0127930 A1 | 7/2004 | Bonutti |
| 2004/0133276 A1 | 7/2004 | Lang et al. |
| 2004/0133280 A1 | 7/2004 | Trieu |
| 2004/0138689 A1 | 7/2004 | Bonutti |
| 2004/0138690 A1 | 7/2004 | Bonutti |
| 2004/0143285 A1 | 7/2004 | Bonutti |
| 2004/0147811 A1 | 7/2004 | Diederich et al. |
| 2004/0153114 A1 | 8/2004 | Reiley et al. |
| 2004/0153115 A1 | 8/2004 | Reiley et al. |
| 2004/0167561 A1 | 8/2004 | Boucher et al. |
| 2004/0167562 A1 | 8/2004 | Osorio et al. |
| 2004/0167563 A1 | 8/2004 | Fogarty et al. |
| 2004/0175408 A1 | 9/2004 | Chun et al. |
| 2004/0186504 A1 | 9/2004 | Schulter et al. |
| 2004/0186576 A1 | 9/2004 | Biscup et al. |
| 2004/0215219 A1 | 10/2004 | Eldridge et al. |
| 2004/0220669 A1 | 11/2004 | Studer |
| 2004/0220673 A1 | 11/2004 | Pria |
| 2004/0220674 A1 | 11/2004 | Pria |
| 2004/0230218 A1 | 11/2004 | Criscuolo et al. |
| 2004/0232589 A1 | 11/2004 | Kawabata et al. |
| 2004/0236425 A1 | 11/2004 | Huang |
| 2004/0243170 A1 | 12/2004 | Suresh et al. |
| 2004/0247641 A1 | 12/2004 | Felt et al. |
| 2004/0254625 A1* | 12/2004 | Stephens .......... A61B 17/12022 623/1.1 |
| 2004/0267315 A1 | 12/2004 | Wolf et al. |
| 2005/0015140 A1 | 1/2005 | deBeer |
| 2005/0015154 A1 | 1/2005 | Lindsey et al. |
| 2005/0018762 A1 | 1/2005 | Aiello et al. |
| 2005/0027358 A1 | 2/2005 | Suddaby |
| 2005/0043808 A1 | 2/2005 | Felt et al. |
| 2005/0090852 A1 | 4/2005 | Layne et al. |
| 2005/0090901 A1 | 4/2005 | Studer |
| 2005/0113937 A1 | 5/2005 | Binette et al. |
| 2005/0113938 A1 | 5/2005 | Jamiolkowski et al. |
| 2005/0119662 A1 | 6/2005 | Reiley et al. |
| 2005/0131267 A1 | 6/2005 | Talmadge |
| 2005/0131268 A1 | 6/2005 | Talmadge |
| 2005/0131269 A1 | 6/2005 | Talmadge |
| 2005/0143836 A1 | 6/2005 | Steinberg |
| 2005/0149191 A1 | 7/2005 | Cragg et al. |
| 2005/0177244 A1 | 8/2005 | Steinberg |
| 2005/0187624 A1 | 8/2005 | Corbitt |
| 2005/0209629 A1 | 9/2005 | Kerr et al. |
| 2005/0229433 A1 | 10/2005 | Cachia |
| 2005/0234498 A1 | 10/2005 | Gronemeyer et al. |
| 2005/0245938 A1 | 11/2005 | Kochan |
| 2005/0245961 A1 | 11/2005 | Mollenauer et al. |
| 2005/0251195 A1 | 11/2005 | Wang |
| 2005/0251245 A1 | 11/2005 | Sieradzki et al. |
| 2005/0261722 A1 | 11/2005 | Crocker et al. |
| 2005/0273075 A1 | 12/2005 | Krulevitch et al. |
| 2005/0278025 A1 | 12/2005 | Ku et al. |
| 2006/0002967 A1 | 1/2006 | Smestad et al. |
| 2006/0025785 A1 | 2/2006 | Cully et al. |
| 2006/0058829 A1* | 3/2006 | Sampson ................ A61F 5/003 606/192 |
| 2006/0064169 A1 | 3/2006 | Ferree |
| 2006/0069403 A1 | 3/2006 | Shalon et al. |
| 2006/0074879 A1 | 4/2006 | Covington et al. |
| 2006/0085022 A1 | 4/2006 | Hayes et al. |
| 2006/0085023 A1 | 4/2006 | Davies et al. |
| 2006/0085024 A1 | 4/2006 | Pepper et al. |
| 2006/0085080 A1 | 4/2006 | Bechgaard et al. |
| 2006/0095064 A1 | 5/2006 | Scribner et al. |
| 2006/0100475 A1 | 5/2006 | White et al. |
| 2006/0100629 A1 | 5/2006 | Lee |
| 2006/0106361 A1 | 5/2006 | Muni et al. |
| 2006/0147492 A1 | 7/2006 | Hunter et al. |
| 2006/0149380 A1 | 7/2006 | Lotz et al. |
| 2006/0173484 A1 | 8/2006 | Solomon |
| 2006/0182780 A1 | 8/2006 | Riley et al. |
| 2006/0205992 A1 | 9/2006 | Lubock et al. |
| 2006/0229631 A1 | 10/2006 | Reiley et al. |
| 2006/0233852 A1 | 10/2006 | Milbocker |
| 2006/0235460 A1 | 10/2006 | Reiley et al. |
| 2006/0241765 A1 | 10/2006 | Burn et al. |
| 2006/0241766 A1 | 10/2006 | Felton et al. |
| 2006/0253200 A1 | 11/2006 | Bao et al. |
| 2006/0276819 A1 | 12/2006 | Osorio et al. |
| 2006/0287665 A1 | 12/2006 | Burton et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0021769 A1 | 1/2007 | Scribner et al. |
| 2007/0038292 A1 | 2/2007 | Danielpour |
| 2007/0038300 A1 | 2/2007 | Bao et al. |
| 2007/0049961 A1 | 3/2007 | Tsou et al. |
| 2007/0055300 A1 | 3/2007 | Osorio et al. |
| 2007/0055380 A1 | 3/2007 | Berelsman et al. |
| 2007/0060941 A1 | 3/2007 | Reiley et al. |
| 2007/0078477 A1* | 4/2007 | Heneveld, Sr. .... A61B 17/0218 606/191 |
| 2007/0100458 A1 | 5/2007 | Pria |
| 2007/0118171 A1 | 5/2007 | Reiley et al. |
| 2007/0118218 A1 | 5/2007 | Hooper |
| 2007/0135921 A1 | 6/2007 | Park |
| 2007/0150059 A1 | 6/2007 | Ruberte et al. |
| 2007/0156246 A1 | 7/2007 | Meswania et al. |
| 2007/0162067 A1 | 7/2007 | Lunsford et al. |
| 2007/0167973 A1 | 7/2007 | Stupecky et al. |
| 2007/0186939 A1 | 8/2007 | Farmache |
| 2007/0190108 A1 | 8/2007 | Datta et al. |
| 2007/0198022 A1 | 8/2007 | Lang et al. |
| 2007/0213760 A1 | 9/2007 | Hayes et al. |
| 2007/0225705 A1 | 9/2007 | Osorio et al. |
| 2007/0225810 A1 | 9/2007 | Colleran et al. |
| 2007/0270953 A1 | 11/2007 | Trieu |
| 2007/0299455 A1 | 12/2007 | Stevens et al. |
| 2007/0299460 A9 | 12/2007 | Boucher et al. |
| 2008/0004596 A1 | 1/2008 | Yun et al. |
| 2008/0015626 A1 | 1/2008 | Keith et al. |
| 2008/0027470 A1 | 1/2008 | Hart et al. |
| 2008/0033471 A1 | 2/2008 | Paz et al. |
| 2008/0045994 A1 | 2/2008 | Rehnke |
| 2008/0051818 A1 | 2/2008 | Phan et al. |
| 2008/0051819 A1 | 2/2008 | Chasmawala et al. |
| 2008/0051825 A1 | 2/2008 | Reiley et al. |
| 2008/0058823 A1 | 3/2008 | Reiley et al. |
| 2008/0058824 A1 | 3/2008 | Reiley et al. |
| 2008/0058828 A1 | 3/2008 | Reiley et al. |
| 2008/0058855 A1 | 3/2008 | Reiley et al. |
| 2008/0058857 A1 | 3/2008 | Reiley et al. |
| 2008/0058943 A1 | 3/2008 | Reiley et al. |
| 2008/0065089 A1 | 3/2008 | Osorio et al. |
| 2008/0065137 A1 | 3/2008 | Boucher et al. |
| 2008/0065138 A1 | 3/2008 | Reiley et al. |
| 2008/0065139 A1 | 3/2008 | Scribner et al. |
| 2008/0065142 A1 | 3/2008 | Reiley et al. |
| 2008/0065143 A1 | 3/2008 | Reiley et al. |
| 2008/0065190 A1 | 3/2008 | Osorio et al. |
| 2008/0065229 A1 | 3/2008 | Adams |

(56) References Cited

U.S. PATENT DOCUMENTS

| | | |
|---|---|---|
| 2008/0071385 A1 | 3/2008 | Binette et al. |
| 2008/0086133 A1 | 4/2008 | Kuslich et al. |
| 2008/0103518 A1 | 5/2008 | Karmon |
| 2008/0132934 A1 | 6/2008 | Reiley et al. |
| 2008/0132935 A1 | 6/2008 | Osorio et al. |
| 2008/0140079 A1 | 6/2008 | Osorio et al. |
| 2008/0140083 A1 | 6/2008 | Reiley et al. |
| 2008/0140084 A1 | 6/2008 | Osorio et al. |
| 2008/0154233 A1 | 6/2008 | Yao et al. |
| 2008/0172081 A1 | 7/2008 | Reiss et al. |
| 2008/0172126 A1 | 7/2008 | Reynolds |
| 2008/0195112 A1 | 8/2008 | Liu et al. |
| 2008/0195207 A1 | 8/2008 | Lin et al. |
| 2008/0200989 A1 | 8/2008 | Cachia |
| 2008/0215031 A1 | 9/2008 | Belfort et al. |
| 2008/0221608 A1 | 9/2008 | Betts |
| 2008/0221628 A1 | 9/2008 | Milbocker et al. |
| 2008/0228025 A1 | 9/2008 | Quick |
| 2008/0234820 A1 | 9/2008 | Felt et al. |
| 2008/0241213 A1 | 10/2008 | Chun et al. |
| 2008/0243122 A1 | 10/2008 | Kohm et al. |
| 2008/0249529 A1 | 10/2008 | Zarda et al. |
| 2008/0249603 A1 | 10/2008 | Schwardt et al. |
| 2008/0249604 A1 | 10/2008 | Donovan et al. |
| 2008/0255569 A1 | 10/2008 | Kohm et al. |
| 2008/0255624 A1 | 10/2008 | Arcenio et al. |
| 2008/0269748 A1 | 10/2008 | Justin et al. |
| 2008/0269759 A1 | 10/2008 | Reiley et al. |
| 2008/0269795 A1 | 10/2008 | Reiley et al. |
| 2008/0269796 A1 | 10/2008 | Reiley et al. |
| 2008/0269897 A1 | 10/2008 | Joshi et al. |
| 2008/0275483 A1 | 11/2008 | Makower et al. |
| 2008/0281355 A1 | 11/2008 | Mayer et al. |
| 2008/0294187 A1 | 11/2008 | Krisht |
| 2008/0294205 A1 | 11/2008 | Greenhalgh et al. |
| 2008/0300604 A1 | 12/2008 | Lu et al. |
| 2009/0012618 A1 | 1/2009 | Ahrens et al. |
| 2009/0037148 A1 | 2/2009 | Lin et al. |
| 2009/0043344 A1 | 2/2009 | Schlotterback |
| 2009/0048623 A1 | 2/2009 | Lafosse et al. |
| 2009/0048683 A1 | 2/2009 | Morris et al. |
| 2009/0048684 A1 | 2/2009 | Lesh |
| 2009/0062871 A1 | 3/2009 | Chin et al. |
| 2009/0076318 A1 | 3/2009 | Li |
| 2009/0076517 A1 | 3/2009 | Reiley et al. |
| 2009/0082872 A1 | 3/2009 | Beger |
| 2009/0082874 A1 | 3/2009 | Cachia |
| 2009/0088788 A1 | 4/2009 | Mouw |
| 2009/0088789 A1 | 4/2009 | O'Neil et al. |
| 2009/0088846 A1 | 4/2009 | Myung et al. |
| 2009/0101157 A1 | 4/2009 | Karmon |
| 2009/0104586 A1 | 4/2009 | Cardoso et al. |
| 2009/0105527 A1 | 4/2009 | Connors et al. |
| 2009/0105732 A1 | 4/2009 | Yurek et al. |
| 2009/0105745 A1 | 4/2009 | Culbert |
| 2009/0112214 A1 | 4/2009 | Philippon et al. |
| 2009/0112323 A1 | 4/2009 | Hestad et al. |
| 2009/0131952 A1 | 5/2009 | Schumacher et al. |
| 2009/0157084 A1 | 6/2009 | Aalsma et al. |
| 2009/0157087 A1 | 6/2009 | Wei et al. |
| 2009/0177206 A1 | 7/2009 | Lozier et al. |
| 2009/0182368 A1 | 7/2009 | Lunsford et al. |
| 2009/0187252 A1 | 7/2009 | Howald et al. |
| 2009/0201700 A1 | 8/2009 | Aso et al. |
| 2009/0234457 A1 | 9/2009 | Lotz et al. |
| 2009/0281630 A1 | 11/2009 | Delince et al. |
| 2009/0306778 A1 | 12/2009 | Marvel |
| 2009/0312807 A1 | 12/2009 | Boudreault et al. |
| 2010/0023126 A1 | 1/2010 | Grotz |
| 2010/0023127 A1 | 1/2010 | Shohat |
| 2010/0069947 A1 | 3/2010 | Sholev et al. |
| 2010/0082036 A1 | 4/2010 | Reiley et al. |
| 2010/0114318 A1 | 5/2010 | Gittings et al. |
| 2010/0121445 A1 | 5/2010 | Corbitt |
| 2010/0137923 A1 | 6/2010 | Greenhalgh et al. |
| 2010/0168755 A1 | 7/2010 | Reiley et al. |
| 2010/0191332 A1 | 7/2010 | Euteneuer et al. |
| 2010/0217399 A1 | 8/2010 | Groh |
| 2010/0256766 A1 | 10/2010 | Hibri et al. |
| 2010/0292798 A1 | 11/2010 | Maestretti |
| 2011/0004307 A1 | 1/2011 | Ahn |
| 2011/0054408 A1 | 3/2011 | Wei et al. |
| 2011/0082547 A1 | 4/2011 | Corbitt |
| 2011/0082552 A1 | 4/2011 | Wistrom et al. |
| 2011/0125158 A1 | 5/2011 | Diwan et al. |
| 2011/0144688 A1 | 6/2011 | Reiss et al. |
| 2011/0152913 A1 | 6/2011 | Jones et al. |
| 2011/0270393 A1 | 11/2011 | Marvel |
| 2011/0295226 A1 | 12/2011 | Shohat et al. |
| 2011/0295370 A1 | 12/2011 | Suh et al. |
| 2011/0295379 A1 | 12/2011 | Shohat |
| 2012/0165941 A1 | 6/2012 | Rabiner et al. |
| 2012/0179251 A1 | 7/2012 | Corbitt |
| 2012/0253097 A1 | 10/2012 | Shohat et al. |
| 2012/0316645 A1 | 12/2012 | Grotz |
| 2013/0018479 A1 | 1/2013 | Grotz |
| 2013/0116794 A1 | 5/2013 | Shohat et al. |
| 2013/0325128 A1 | 12/2013 | Perloff et al. |
| 2013/0331946 A1 | 12/2013 | Shohat |
| 2014/0031939 A1 | 1/2014 | Wolfe et al. |
| 2014/0052250 A1 | 2/2014 | Wirtel, III et al. |
| 2014/0058432 A1 | 2/2014 | Scribner et al. |
| 2014/0066939 A1 | 3/2014 | Kaiser et al. |
| 2014/0074245 A1 | 3/2014 | Shohat et al. |
| 2014/0128974 A1 | 5/2014 | Bramer |
| 2014/0128978 A1 | 5/2014 | Suh et al. |
| 2014/0142710 A1 | 5/2014 | Lang |
| 2014/0296987 A1 | 10/2014 | Shohat |
| 2014/0303730 A1 | 10/2014 | McGuire et al. |
| 2014/0343675 A1 | 11/2014 | Vanleeuwen et al. |
| 2014/0371864 A1 | 12/2014 | Shohat |
| 2014/0378980 A1 | 12/2014 | Lomeli et al. |
| 2015/0127104 A1 | 5/2015 | Levy et al. |
| 2015/0289988 A1 | 10/2015 | Ashley et al. |
| 2015/0320570 A1 | 11/2015 | Suh et al. |
| 2015/0351914 A1 | 12/2015 | Bromer |
| 2016/0058548 A1 | 3/2016 | Grotz |
| 2016/0095706 A1 | 4/2016 | Grotz |
| 2016/0120654 A1 | 5/2016 | Hibri et al. |
| 2016/0199189 A1 | 7/2016 | Shohat |
| 2016/0199197 A1 | 7/2016 | Wolfe et al. |
| 2016/0235443 A1 | 8/2016 | Kaiser et al. |
| 2016/0310286 A1 | 10/2016 | McJunkin |
| 2016/0354182 A1 | 12/2016 | Karmon |
| 2017/0042698 A1 | 2/2017 | Saidha et al. |
| 2017/0119535 A1 | 5/2017 | Teisen et al. |
| 2017/0312088 A1 | 11/2017 | Grotz |
| 2018/0000603 A1 | 1/2018 | Shohat |
| 2018/0028319 A1 | 2/2018 | Grotz |
| 2018/0028326 A1 | 2/2018 | Vanleeuwen et al. |
| 2018/0221163 A1 | 8/2018 | Hibri |
| 2019/0029841 A1 | 1/2019 | Suh et al. |
| 2019/0038416 A1 | 2/2019 | Grotz |

FOREIGN PATENT DOCUMENTS

| | | |
|---|---|---|
| CN | 2776338 | 5/2006 |
| DE | 102007018341 | 10/2008 |
| DE | 102007051782 | 5/2009 |
| EP | 0441516 A2 | 8/1991 |
| EP | 0507645 | 10/1992 |
| EP | 0617930 A1 | 10/1994 |
| EP | 1219265 A2 | 7/2002 |
| EP | 1635738 A2 | 3/2006 |
| JP | 06-510450 | 11/1994 |
| JP | 10-504202 | 4/1998 |
| JP | 2002-191609 | 7/2002 |
| JP | 2002-360700 | 12/2002 |
| JP | 2003-325685 | 11/2003 |
| JP | 2006-247257 | 9/2006 |
| WO | WO 93/04727 | 3/1993 |
| WO | 9425078 A1 | 11/1994 |
| WO | 9513762 A1 | 5/1995 |
| WO | WO 95/33502 | 12/1995 |

(56) References Cited

FOREIGN PATENT DOCUMENTS

| WO | 9640023 A1 | 12/1996 |
|---|---|---|
| WO | 9640024 A1 | 12/1996 |
| WO | 9719653 A1 | 6/1997 |
| WO | 9826737 A1 | 6/1998 |
| WO | 9903454 A1 | 1/1999 |
| WO | 9915116 A1 | 4/1999 |
| WO | 0013624 A2 | 3/2000 |
| WO | 0044808 A1 | 8/2000 |
| WO | 0113832 A1 | 3/2001 |
| WO | 0113833 A1 | 3/2001 |
| WO | WO 02/085263 | 10/2002 |
| WO | WO 03/028572 | 4/2003 |
| WO | 03105917 A2 | 12/2003 |
| WO | WO 2004/043303 | 5/2004 |
| WO | 2004112656 A2 | 12/2004 |
| WO | WO 2005/105172 | 11/2005 |
| WO | WO 2006/001009 | 1/2006 |
| WO | WO 2006/055516 | 5/2006 |
| WO | WO 2006/074879 | 7/2006 |
| WO | WO 2006/091660 | 8/2006 |
| WO | WO 2007/002561 | 1/2007 |
| WO | WO 2007/054934 | 5/2007 |
| WO | WO 2007/125060 | 11/2007 |
| WO | WO 2008/111073 | 9/2008 |
| WO | WO 2008/111078 | 9/2008 |
| WO | WO 2008/139473 | 11/2008 |
| WO | WO 2008/157727 | 12/2008 |
| WO | WO 2012/017438 | 2/2012 |

OTHER PUBLICATIONS

Communication Pursuant to Article 94(3) EPC dated Dec. 3, 2014 From the European Patent Office Re. Application No. 08719972.5.
Office Action dated May 26, 2014 From the State Intellectual Property Office of the People's Republic of China Re. Application No. 200880015430.3 and Its Translation Into English.
Search Report dated May 26, 2014 From the State Intellectual Property Office of the People's Republic of China Re. Application No. 200880015430.3 and Its Translation Into English.
First Office Action in Chinese Application No. 201410696820.9, dated Dec. 30, 2015, 7 pages.
Official Action in Japanese Application No. 2013-99793, dated Jun. 3, 2016, 6 pages.
European Search Report in European Application No. 16177165, dated Oct. 13, 2016, 6 pages.
Invitation to Pay Additional Fees dated Sep. 17, 2008 From the International Searching Authority Re. Application No. PCT/IL08/00354.
Applicant-Initiated Interview Summary dated Feb. 15, 2013 From the US Patent and Trademark Office Re. U.S. Appl. No. 12/531,332.
Communication Pursuant to Article 94(3) EPC dated Dec. 1, 2011 From the European Patent Office Re. Application No. 05754685.5.
Communication Pursuant to Article 94(3) EPC dated Feb. 16, 2012 From the European Patent Office Re. Application No. 08738353.5.
Communication Pursuant to Article 94(3) EPC dated Dec. 21, 2012 From the European Patent Office Re. Application No. 08738353.5.
Communication Pursuant to Rule 70(2) and 70a(2) EPC dated May 24, 2013 From the European Patent Office Re. Application No. 08719972.5.
Communication Pursuant to Rules 70(2) and 70a(2) EPC dated Jun. 24, 2011 From the European Patent Office Re. Application No. 08738353.5.
Communication Relating to the Results of the Partial International Search dated Nov. 3, 2011 From the International Searching Authority Re. Application No. PCT/IL2011/000637.
Communication Relating to the Results of the Partial International Search dated Nov. 18, 2005 From the International Searching Authority Re.: Application No. PCT/IL2005/000672.
Examiner's Report dated Apr. 28, 2010 From the Australian Government, IP Australia Re. Application No. 2005257050.
International Preliminary Report on Patentability dated Feb. 14, 2013 From the International Bureau of WIPO Re. Application No. PCT/IL2011/000637.
International Preliminary Report on Patentability dated Jan. 21, 2010 From the International Bureau of WIPO Re.: Application No. PCT/IL2008/000347.
International Preliminary Report on Patentability dated Oct. 22, 2009 From the International Bureau of WIPO Re.: Application No. PCT/IL2008/000354.
International Search Report and the Written Opinion dated Jan. 9, 2012 From the International Searching Authority Re. Application No. PCT/IL2011/000637.
International Search Report dated Nov. 20, 2008 From the International Searching Authority Re.: Application No. PCT/IL08/00347.
International Search Report dated Feb. 22, 2006 From the International Searching Authority Re.: Application No. PCT/IL2005/000672.
International Search Report dated Nov. 26, 2008 From the International Searching Authority Re.: Application No. PCT/IL08/00354.
Invitation to Pay Additional Fees dated Sep. 23, 2008 From the International Searching Authority Re.: Application No. PCT/IL08/00347.
Notice of Allowance dated Feb. 3, 2014 From the US Patent and Trademark Office Re. U.S. Appl. No. 12/531,332.
Notice of Allowance dated Mar. 8, 2013 From the US Patent and Trademark Office Re. U.S. Appl. No. 15/599,823.
Notice of Allowance dated Mar. 14, 2012 From the US Patent and Trademark Office Re.: U.S. Appl. No. 11/630,257.
Notice of Reason for Rejection dated Mar. 14, 2014 From the Japanese Patent Office Re. Application No. 2013-99793 and Its Translation Into English.
Notification of Publication of Patent Application for Invention and Entering the Substantive Examination Proceeding dated Oct. 13, 2010 From the Patent Office of the People's Republic of China Re. Application No. 200880015430.3.
Notification of Publication of Patent Application for Invention and Entering the Substantive Examination Proceeding dated Jul. 28, 2010 From the Patent Office of the People's Republic of China Re. Application No. 200880024447.5 and Its Translation Into English.
Office Action dated Jun. 10, 2013 From the Israel Patent Office Re. Application No. 200939 and Its Translation Into English.
Office Action dated Nov. 18, 2012 From the Israel Patent Office Re.: Application No. 180270 and Its Translation Into English.
Office Action dated Nov. 20, 2012 From the Israel Patent Office Re. Application No. 200939 and Its Translation Into English.
Office Action dated Feb. 26, 2014 From the Israel Patent Office Re. Application No. 200939 and Its Translation Into English.
Office Action dated Oct. 27, 2009 From the Israel Patent Office Re.: Application No. 180270 and Its Translation Into English.
Office Action dated Jan. 28, 2014 From the State Intellectual Property Office of the People's Republic of China Re. Application No. 200880015430.3.
Office Action dated Oct. 30, 2013 From the Israel Patent Office Re. Application No. 200939 and Its Translation Into English.
Official Action dated Oct. 1, 2012 From the US Patent and Trademark Office Re. U.S. Appl. No. 15/599,823.
Official Action dated Jun. 8, 2009 From the US Patent and Trademark Office Re.: U.S. Appl. No. 11/630,257.
Official Action dated Sep. 11, 2013 From the US Patent and Trademark Office Re. U.S. Appl. No. 12/531,332.
Official Action dated Aug. 13, 2012 From the US Patent and Trademark Office Re. U.S. Appl. No. 12/531,332.
Official Action dated Apr. 14, 2010 From the US Patent and Trademark Office Re.: U.S. Appl. No. 11/630,257.
Official Action dated Feb. 14, 2013 From the US Patent and Trademark Office Re. U.S. Appl. No. 12/764,238.
Official Action dated Apr. 15, 2013 From the US Patent and Trademark Office Re. U.S. Appl. No. 12/531,073.
Official Action dated Aug. 19, 2009 From the US Patent and Trademark Office Re.: U.S. Appl. No. 11/630,257.
Official Action dated Jul. 19, 2013 From the US Patent and Trademark Office Re. U.S. Appl. No. 13/811,069.

(56) References Cited

OTHER PUBLICATIONS

Official Action dated Feb. 22, 2013 From the US Patent and Trademark Office Re. U.S. Appl. No. 12/531,332.
Official Action dated Oct. 31, 2012 From the US Patent and Trademark Office Re. U.S. Appl. No. 12/531,073.
Patent Examination Report dated Jul. 13, 2012 From the Australian Government, IP Australia Re. Application No. 2008224435.
Patent Examination Report dated Aug. 29, 2013 From the Australian Government, IP Australia Re. Application No. 2008224435.
Patentability Search on Expandable Prostheses Particularly Useful for Rotator Cuff Protection dated Oct. 31, 2007 Effectuated by Sol Sheinbein.
Requisition by the Examiner dated Apr. 30, 2014 From the Canadian Intellectual Property Office Re. Application No. 2,680,812.
Restriction Official Action dated Dec. 12, 2011 From the US Patent and Trademark Office Re. U.S. Appl. No. 12/531,073.
Restriction Official Action dated May 23, 2013 From the US Patent and Trademark Office Re. U.S. Appl. No. 13/811,069.
Restriction Official Action dated Sep. 24, 2012 From the US Patent and Trademark Office Re. U.S. Appl. No. 12/764,238.
Supplementary European Search Report and the European Search Opinion dated Jun. 6, 2011 From the European Patent Office Re. Application No. 08738353.5.
Supplementary European Search Report and the European Search Opinion dated May 6, 2013 From the European Patent Office Re. Application No. 08719972.5.
Third Party Submission Under 37 CFR §1.99 Dated Mar. 26, 2010 in the US Patent and Trademark Office Re. U.S. Appl. No. 12/531,332.
Translation of Decision on Rejection dated Oct. 16, 2009 From the State Intellectual Property Office of the People's Republic of China Re.: Application No. 200580028684.5.
Translation of Notice of Payment of the Restoration Fee for Unity of Invention dated Jul. 26, 2011 From the State Intellectual Property Office of the People's Republic of China Re. Application No. 200880014369.0.
Translation of Notice of Reason for Rejection dated Nov. 5, 2010 From the Japanese Patent Office Re. Application No. 2007-517651.
Translation of Notice of Reason for Rejection dated Nov. 27, 2012 From the Japanese Patent Office Re. Application No. 2009-553278.
Translation of Office Action dated Jul. 3, 2009 From the State Intellectual Property Office of the People's Republic of China Re.: Application No. 200580028684.5.
Translation of Office Action dated Dec. 11, 2012 From the State Intellectual Property Office of the People's Republic of China Re. Application No. 200880015430.3.
Translation of Office Action dated Jan. 11, 2011 From the State Intellectual Property Office of the People's Republic of China Re. Application No. 200580028684.5.
Translation of Office Action dated Jul. 11, 2013 From the State Intellectual Property Office of the People's Republic of China Re. Application No. 200880015430.3.
Translation of Office Action dated Feb. 17, 2012 From the State Intellectual Property Office of the People's Republic of China Re. Application No. 200880015430.3.
Translation of Office Action dated Oct. 19, 2011 From the State Intellectual Property Office of the People's Republic of China Re. Application No. 200880014369.0.
Translation of Office Action dated Mar. 28, 2012 From the State Intellectual Property Office of the People's Republic of China Re. Application No. 200880014369.0.
Translation of Office Action dated Mar. 30, 2012 From the State Intellectual Property Office of the People's Republic of China Re. Application No. 200880024447.5.
Translation of Office Action dated Oct. 31, 2008 From the State Intellectual Property Office of the People's Republic of China Re.: Application No. 200580028684.5.
Translation of Official Copy of Decision of Rejection dated Jun. 7, 2011 From the Japanese Patent Office Re. Application No. 2007-517651.
Translation of Search Report dated Jul. 11, 2013 From the State Intellectual Property Office of the People's Republic of China Re. Application No. 200880015430.3.
Written Opinion dated Nov. 20, 2008 From the International Searching Authority Re.: Application No. PCT/IL08/00347.
Written Opinion dated Feb. 22, 2006 From the International Searching Authority Re.: Application No. PCT/IL2005/000672.
Written Opinion dated Nov. 26, 2008 From the International Searching Authority Re.: Application No. PCT/IL08/00354.
Anderson "Biological Responses to Materials", Annual Review of Materials Research, 31: 81-110, 2001.
Third Office Action in Chinese Application No. 201410696820.9, dated Jan. 25, 2017, 12 pages (with English translation).
International Search Report and Written Opinion issued in connection with International Application No. PCT/IB2012/002088 dated Mar. 1, 2013, 8 pages.
International Preliminary Report on Patentability issued in connection with International Application No. PCT/IB2012/002088 dated Jun. 30, 2015, 7 pages.
European Search Report in European Application No. 08719979 dated Dec. 22, 2015, 3 pages.
International Preliminary Report on Patentability dated Jan. 21, 2010 From the International Bureau of WIPO Re.: Application No. PCT/IL2008/000662.
International Preliminary Report on Patentability dated Jul. 27, 2006 From the International Preliminary Examining Authority Re.: Application No. PCT/IL2005/000672.
International Search Report and the Written Opinion dated Oct. 23, 2008 From the International Searching Authority Re.: Application No. PCT/IL08/00662.
International Search Report dated Nov. 14, 2008 From the International Searching Authority Re.: Application No. PCT/IL08/00354.
Request for Reconsideration Filed With an RCE dated Aug. 9, 2010 to Official Action dated Apr. 14, 2010 From the US Patent and Trademark Office Re: U.S. Appl. No. 11/630,257.
Restriction Official Action dated Feb. 6, 2012 From the US Patent and Trademark Office Re. U.S. Appl. No. 12/531,073.

\* cited by examiner

SHOULDER IMPLANT FOR SIMULATING A BURSA

RELATED APPLICATIONS

This application is a continuation of U.S. patent application Ser. No. 12/531,332 filed on Sep. 15, 2009, which is a National Phase of PCT Patent Application No. PCT/IL2008/000347 having International filing date of Mar. 13, 2008, which claims the benefit of priority of U.S. Provisional Patent Application No. 60/918,051 filed on Mar. 15, 2007. The contents of the above applications are all incorporated herein by reference.

FIELD OF INVENTION

The present inventions relate generally to the field of medical devices and the treatment of human medical conditions using the medical devices. More specifically, the present inventions include expandable prosthetic devices used for treating a variety of conditions, including rotator cuff injuries, broken and/or depressed bone fractures, infection and/or inflammation in the body.

BACKGROUND OF THE INVENTION

Through repeated strenuous motion, sensitive soft tissues often suffer wear and tear injuries from repeatedly rubbing against one another and/or hard tissues, such as bone. Tears of rotator cuff tendons and articular capsule disintegration are examples of this type of injury. In addition, these tissues can be adversely affected by inflammation, infection, disease and/or genetic predispositions which lead to degeneration of these tissues.

Other bodily injuries, such as fractures of hollow bones (i.e. having medullar cavities) and depression fractures of vertebra require complex procedures for treatment, for example alignment and fixation of multiple bone fragments for the former and disc replacement for the latter.

Various solutions to problems in treatment of these injuries have been proposed, for example:

U.S. Pat. App. Pub. No. 2007/0198022 to Lang, et al., the disclosure of which is incorporated herein by reference, describes methods, compositions and tools for repairing articular surfaces repair materials and for repairing an articular surface. The articular surface repairs are customizable or highly selectable by patient and geared toward providing optimal fit and function. The surgical tools are designed to be customizable or highly selectable by patient to increase the speed, accuracy and simplicity of performing total or partial arthroplasty.

JP Pat. App. Pub. No. 2006-247257 to Yasuhiko, et al., the disclosure of which is incorporated herein by reference, describes a bone cement injector which is equipped with an injection tube and a balloon detachably mounted on one end of the injection tube, where the balloon is formed with a bioabsorptive material. Using the bone cement injector of this invention, the balloon is inserted into the damaged section of the vertebra to be treated, and subsequently the bone cement is injected into this balloon. Thereby, the bone cement can be injected into the corpus vertebra of the damaged part of the vertebra while preventing the blood from mixing in the bone cement and the bone cement from leaking into the vertebral canal.

U.S. Pat. App. Pub. No. 2005/0245938 to Kochan, the disclosure of which is incorporated herein by reference, describes a device for repair of intervertebral discs and cartilages in articular joints includes a catheter for inserting through a cannula, the catheter having a distal end and a proximal end and a lumen extending longitudinally therethrough. An expandable balloon may optionally be detachably attached to the catheter near the distal end. The proximal end of the catheter is coupled to an injector that holds a supply of a thermoplastic elastomer material at a predetermined elevated temperature sufficiently high to maintain the thermoplastic elastomer at a liquid state. The device allows a thermoplastic elastomer material to be injected into the intervertegral disc space or the articular joint space as a replacement prosthetic for the disc's nucleus pulposus or the joint's cartilage. This procedure is carried out percutaneously through the cannula.

U.S. Pat. No. 6,755,862 to Keynan, the disclosure of which is incorporated herein by reference, describes an intramedullary support strut for a long bone for a range of different applications including anchoring and fixation. The strut is in the form of nested telescopic members. In the retracted configuration, the strut is compact and may be inserted into position aligned with a shaft made in the medullary canal via a portal made in the lateral cortex of the bone. The strut may then be telescopically extended into the medullary canal to provide the required support.

U.S. Pat. No. 6,613,052 to Kinnett, the disclosure of which is incorporated herein by reference, describes an apparatus developed to enable a surgeon to perform multiple orthopedic surgical operations, such as orthopedic surgical resectioning, total joint replacement and fixation of fractures, based on a single reference point. The apparatus is adjustable to conform to the needs and dimensions of individual patients and the surgical procedure(s) to be performed. The apparatus includes a support adapted for insertion into and alignment within the medullary cavity of a patient's bone. The support is capable of expanding into the bone so that the support is fixed within the bone and alignable to the bone. The support may be implanted to align a fractured bone, or extend a distance beyond its fixed position within the medullary cavity to provide a known surgical reference point. The apparatus includes one or more cutting guides mountable on the support and used in performing the desired surgical procedure(s). The cutting guides are positionable with respect to the known surgical reference point created by the support which enables the user to accurately position and secure various instruments at the desired position about the patient's anatomy.

SUMMARY OF THE INVENTION

An aspect of some embodiments of the invention relates to prostheses adapted to reduce injuries between soft tissues of the body and other tissues. In an embodiment of the invention, soft tissues are for example, tendons and/or ligaments. In an embodiment of the invention, other tissues are, for example, bones. In an embodiment of the invention, the prosthesis is expandable. Optionally, the prosthesis is elastic. In some embodiments of the invention, the prosthesis is rigid. In an embodiment of the invention, the prosthesis is shaped and/or sized to simulate a bursa naturally occurring in the body. Optionally, the bursa simulated is the one expected to be present at the implantation site of the prosthesis in a healthy patient.

In an embodiment of the invention, an expandable prosthesis adapted to reduce and/or eliminate injury to the rotator cuff. Optionally, the expandable prosthesis is sponge-like. Optionally, the expandable prosthesis is inflatable. In some exemplary embodiments of the invention, the expandable prosthesis is adapted to be inserted between the tendons of the rotator cuff and the acromion and/or coracoid process. Expandable prosthesis is biocompatible and/or biodegradable, in an exemplary embodiment of the invention. Optionally, the expandable prosthesis is adapted to elute pharmaceutical agents once implanted in a patient's body. In an embodiment of the invention, inflatable expandable prosthesis is inflated with filler, for example a gas, liquid, and/or gel. Optionally, the filler is biocompatible and/or biodegradable. In some embodiments of the invention, the prosthesis is only partially filled.

In some embodiments of the invention, the prosthesis is provided with anchoring devices adapted to maintain the prosthesis in a steady relationship with the anatomical features around the implantation site. Optionally, the prosthesis is contoured along its exterior to accommodate anatomical features around the implantation site.

An aspect of some embodiments of the invention relates to a method for implanting an expandable prosthesis adapted to reduce and/or eliminate injury between soft tissues of the body and other tissues, for example to the rotator cuff. In an embodiment of the invention, the expandable prosthesis is either sponge-like or inflatable and is expanded in a space between the tendons of the rotator cuff and the acromion and/or coracoid process. In some embodiments of the invention, a prosthesis implantation and/or inflation device is used to implant and/or inflate the expandable prosthesis.

An aspect of some embodiments of the invention relates to an expandable prosthesis for the alignment of bone fragments which is provided with walls thick enough to withstand the stresses of normal activity while still maintaining the bone fragments in alignment. In an embodiment of the invention, the expandable prosthesis is inflatable. In some exemplary embodiments of the invention, the expandable prosthesis is adapted to be inserted into the medullar cavity of a plurality of bone fragments. Expandable prosthesis is biocompatible and/or biodegradable, in an exemplary embodiment of the invention. Optionally, the expandable prosthesis is adapted to elute pharmaceutical agents once implanted in a patient's body. In an embodiment of the invention, inflatable expandable prosthesis is inflated with filler, for example a gas, liquid, cement and/or gel, to provide sufficient rigidity to expandable prosthesis to align a plurality of bone fragments. Optionally, the filler is biocompatible and/or biodegradable.

In some embodiments of the invention, the prosthesis is provided with a calibration kit which is designed to determine the size and/or shape of the medullar cavity of the bone fragments and/or to choose an appropriate sized prosthesis for implantation into the cavity.

An aspect of some embodiments of the invention relates to a method for aligning bone fragments using an inflatable, expandable prosthesis. In an embodiment of the invention, an inflatable, expandable prosthesis is introduced into the medullar channel of a plurality of bone fragments. In some embodiments of the invention, a prosthesis implantation and/or inflation device is used to implant and/or inflate the expandable prosthesis. Optionally, pharmaceutical agents are eluted into the patient by the expandable prosthesis.

An aspect of some embodiments of the invention relates to an expandable prosthesis for treating inflammation and/or infection. Optionally, the expandable prosthesis is a sponge-like structure, sponge-like being defined as including at least one of the following properties: porous, absorbent and/or compressible. Optionally, the expandable prosthesis is inflatable. Expandable prosthesis is biocompatible and/or biodegradable, in an exemplary embodiment of the invention. Optionally, the expandable prosthesis is adapted to elute pharmaceutical agents once implanted in a patient's body. Expandable sponge-like device optionally contains within its cavities at least one biocompatible and/or biodegradable gelling material that expands when it comes into contact with at least one bodily fluid, for example by absorbing water.

In an embodiment of the invention, inflatable expandable prosthesis is inflated with filler, for example a gas, liquid, and/or gel. Optionally, the filler is biocompatible and/or biodegradable and/or contains the pharmaceutical agents. In some embodiments, elution of pharmaceutical agents is according to a schedule timed with the biodegradable properties of the expandable prosthesis.

An aspect of some embodiments of the invention, relates to an expandable prosthesis for treating depressed fractures. In some embodiments of the invention, the expandable prosthesis comprises an inner section and an external section. Optionally, at least one section of the expandable prosthesis is sponge-like. The at least one sponge-like section optionally contains within its cavities at least one biocompatible and/or biodegradable gelling material that expands when it comes into contact with at least one bodily fluid, for example by absorbing water. Optionally, at least one section of the expandable prosthesis is inflatable. In an embodiment of the invention, the at least one inflatable expandable section is inflated with filler, for example a gas, liquid, cement and/or gel, to provide sufficient rigidity to treat the depressed fracture.

In some exemplary embodiments of the invention, the expandable prosthesis is adapted to be inserted at or near a fractured vertebra. Expandable prosthesis is optionally biocompatible and/or biodegradable, in an exemplary embodiment of the invention. Optionally, the expandable prosthesis is adapted to elute pharmaceutical agents once implanted in a patient's body.

In an embodiment of the invention, at least one section of the prosthesis is inflated with filler, for example a gas, liquid, cement and/or gel. Optionally, the filler is biocompatible and/or biodegradable. In some embodiments of the invention, the expandable prosthesis is adapted to have at least one section removed prior to closing the patient. In an embodiment of the invention, at least one section is adapted to withstand the expected pressures from being implanted at or near a vertebra of the patient. In an embodiment of the invention, the expandable prosthesis is inflated and/or implanted using a plurality of prosthesis inflation and/or implantation devices.

An aspect of some embodiments of the invention relates to a method for treating depressed fractures using an expandable prosthesis. In an embodiment of the invention, the method implants at least one section of an expandable prosthesis comprising a plurality of separately expandable and/or retractable sections. In an embodiment of the invention, at least one section of an expandable prosthesis is used to properly deploy filler for treating the depressed fracture. Optionally, at least one section of the expandable prosthesis is withdrawn from the patient before closing the patient. Optionally, at least one section of the expandable prosthesis is sealed and implanted in the patient. In some embodiments of the invention, pharmaceutical agents are eluted into the patient by the expandable prosthesis.

An aspect of some embodiments of the invention relates to a prosthesis implantation and/or inflation device. In an embodiment of the invention, the prosthesis implantation and/or inflation device includes a syringe adapted to inject filler into an expandable prosthesis, for example through a tube which operatively connects syringe to the expandable prosthesis. In some embodiments of the invention, the syringe is comprised of at least a plunger and a canister. Optionally, the plunger is advanced through the canister by the device in order to inject filler into the prosthesis. Optionally, the canister is advanced against the plunger, which remains relatively fixed due to counterforce from a backstop, in order to inject filler into the prosthesis.

In some exemplary embodiments of the invention, the prosthesis implantation and/or inflation device includes a safety. Optionally, the safety comprises at least a spring and a ball, wherein the ball acts as a counterpart to a groove in the backstop. Excessive force on the backstop by continued advancement of the canister towards the plunger triggers the safety, popping the ball out of the groove and freeing the backstop to move. In an embodiment of the invention, the placement of the backstop is according to a predetermined level of desired inflation of the prosthesis.

There is thus provided in accordance with an embodiment of the invention, a prosthesis for reducing injury to soft tissues of the body, comprising: a member adapted to simulate at least one of a size or a shape of a naturally occurring bursa.

In an embodiment of the invention, the member is expandable. Optionally, the member is adapted to be at least partially inflated. Optionally, the member is inflated sufficiently to reduce rubbing of the soft tissues against other tissues while permitting at least some movement of the soft tissues relative to the other tissues. Optionally, at least some movement of the soft tissues relative to the other tissues is full movement. In an embodiment of the invention, the member is sponge-like. Optionally, the sponge-like member is provided with a fluid absorbent material which when fluids are absorbed induces expansion of the sponge-like expandable member.

In an embodiment of the invention, the prosthesis is constructed of at least one of a biocompatible or biodegradable material. Optionally, the at least one of a biocompatible or biodegradable material is PCL, PGA, PHB, plastarch material, PEEK, zein, PLA, PDO, PLGA, collagen or methyl cellulose.

In an embodiment of the invention, the prosthesis is constructed of at least one non-biodegradable material. Optionally, the at least one non-biodegradable material is polyethylene, polyurethane, silicon, or poly-paraphenylene terephthalamide.

In an embodiment of the invention, the prosthesis further comprises a rigid ring having a lumen therein attached to the member, wherein the lumen provides fluid communication to an inner space of the member.

In an embodiment of the invention, the prosthesis further comprises a plug adapted to lodge in the lumen thereby sealing the inner space of the member. Optionally, the plug is constructed of at least one of a biocompatible or biodegradable material.

In an embodiment of the invention, the member is elastic.

In an embodiment of the invention, the prosthesis further comprises at least one anchoring device for stabilizing the prosthesis upon implantation. Optionally, the at least one anchoring device is constructed of at least one of a biocompatible or biodegradable material.

In an embodiment of the invention, the member is contoured to act as a counterpart to natural anatomical features of an implantation site.

In an embodiment of the invention, adapted to elute at least one pharmaceutical agent.

In an embodiment of the invention, the size of the prosthesis is approximately 2 cm to 10 cm in length along a long axis, approximately 2 cm to 7 cm in length along a short axis and approximately 0.5 mm to 20 mm in height, when expanded.

In an embodiment of the invention, the member is rigid. Optionally, the member is contoured to act as a counterpart to natural anatomical features of an implantation site while permitting at least some movement of the soft tissues relative to other tissues.

In an embodiment of the invention, adapted for reducing injury to a rotator cuff. In an embodiment of the invention, adapted for reducing injury to at least one of a flexor or an extensor. In an embodiment of the invention, adapted for reducing injury between a quadriceps and a femur. In an embodiment of the invention, adapted for reducing injury between a skin and a plantar fascia and a calcaneus of the body. In an embodiment of the invention, injury is at least one of inflammation or infection.

There is further provided in accordance with an exemplary embodiment of the invention, a method for implanting a prosthesis adapted to reduce injury to between soft tissues and other tissues of a body, comprising: placing the prosthesis into an implantation site between the soft tissues and the other tissues; and, simulating with the prosthesis a bursa naturally occurring at the implantation site. In an embodiment of the invention, the method further comprises eluting at least one pharmaceutical agent from the prosthesis at the implantation site. Optionally, placing and simulating occurs without significantly reducing movement of the soft tissues relative to the other tissues. Optionally, the soft tissues are tendons of a rotator cuff and the other tissues are at least one of a humerus, an acromion or a coracoid process.

There is further provided in accordance with an exemplary embodiment of the invention, a prosthesis for the alignment of bone fragments, comprising: a member adapted to be implanted in the medullar cavity of the bone fragments, wherein the member is provided with an outer wall thickness adapted to accommodate at least a minimum level of rigidity necessary to maintain bone fragment alignment during normal activity. In an embodiment of the invention, the prosthesis further comprises a calibration kit adapted to perform at least one of determining the size of the medullar cavity or introducing the proper sized member into the medullar cavity. Optionally, the member is tubular or vasiform in shape. Optionally, at least the member is constructed of at least one of a biocompatible or biodegradable material. Optionally, the member has an approximate outer diameter between 2 mm and 15 mm and an approximate length between 5 cm and 50 cm. Optionally, the prosthesis is adapted to elute at least one pharmaceutical agent.

There is further provided in accordance with an exemplary embodiment of the invention, a method for aligning bone fragments, comprising: introducing a prosthesis into the medullar cavity of a plurality of bone fragments; and, inflating the prosthesis to a sufficient rigidity to hold the bone fragments in alignment during normal activity. In an embodiment of the invention, the method further comprises determining the size of the medullar cavity using a calibration kit.

There is further provided in accordance with an exemplary embodiment of the invention, a prosthesis adapted for treating depressed fractures comprising a plurality of separately expandable and retractable sections. Optionally, the prosthesis comprises an inner section and an outer section, wherein the outer section at least partially surrounds the inner section. Optionally, the inner section is cylindrical and measures approximately 2 cm to 7 cm in diameter and 2 cm to 5 cm in height. Optionally, the inner section and outer section are manufactured from at least one of polyurethane, ultra high molecular weight polyethylene, poly-paraphenylene terephthalamide, PCL, PGA, PHB, plastarch material, PEEK, zein, PLA, PDO and PLGA, collagen, or methyl cellulose.

There is further provided in accordance with an exemplary embodiment of the invention, a method for treating a depressed fracture using a prosthesis comprising a plurality of separately expandable and retractable sections, comprising: introducing the prosthesis to the implantation area, wherein the fracture is concave in relation to the area; inflating an inner section; inflating an outer section; deflating the inner section; and, filling a cavity left by the deflating of the inner section such that support is rendered to the depressed fracture from the filled cavity. Optionally, the inner section is withdrawn prior to filling the cavity.

In an embodiment of the invention, the method further comprises withdrawing the outer section after filling the cavity.

There is further provided in accordance with an exemplary embodiment of the invention, a system for sealing an inflatable prosthesis, comprising: a prosthesis inflation device; a tube operatively connected to the prosthesis near one end and the prosthesis inflation device on the other end; a plug attached to the tube at the prosthesis end of the tube; and, a rigid ring attached to the prosthesis and slidably attached around the tube between the prosthesis inflation device and the plug; wherein pulling the tube towards the prosthesis inflation device causes plug to lodge in the rigid ring, sealing the prosthesis with the plug. Optionally, the plug is attached to the tube by gripping protrusions.

There is further provided in accordance with an exemplary embodiment of the invention, a method of sealing an inflatable prosthesis, comprising: pulling a tube out of the prosthesis and through a rigid ring; and, lodging a plug located on the end of the tube in the rigid ring.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which.

DETAILED DESCRIPTION OF EXEMPLARY EMBODIMENTS

As described above, repeated strenuous motion often causes sensitive soft tissues to suffer wear and tear injuries from repeatedly rubbing against one another and/or hard tissues, such as bone. Tears of tendons and/or ligaments and articular capsule disintegration are examples of this type of injury. In addition, these tissues can be adversely affected by inflammation, infection, disease and/or genetic predispositions which lead to degeneration of these tissues.

Injuries to soft tissues such as tendons can cause pain and impaired function of the area served by the tendon. Typically, a bursa can be found near areas where "friction" injuries due to the rubbing are prone to occur. A bursa is a natural fluid collection that permits movements between tendons and/or ligaments and bone parts and prevents injury to these tendons by acting as a cushion and/or movement facilitator between them.

In some embodiments of the invention, prostheses described herein are shaped and/or sized to simulate the natural bursa found in the intended area of implantation. For example, in some of the rotator cuff embodiments described below, the described exemplary prostheses are shaped and/ or sized to simulate the subacromial bursa. Optionally, the prostheses are sized to supplement a natural bursa which is misshapen and/or undersized, bringing the combination of the natural bursa and the prosthesis into line with the shape and/or size of a healthy bursa.

The rotator cuff is an anatomical term given to the group of muscles and their tendons that act to stabilize the shoulder and to permit rotation and abduction of the arm. Along with the teres major and the deltoid, the four muscles of the rotator cuff make up the six muscles of the human body which connect to the humerus and scapula. Injury to the tendons and/or these muscles can cause pain and impaired function of the shoulder. The subacromial bursa is a natural fluid collection that permits movement of these rotator cuff tendons beneath the acromion and coracoid process, both of which are part of scapula bone. In some rotator cuff injuries, the subacromial bursa becomes inflamed and suffers from a reduced ability to prevent injury to the tendons through friction.

Figure 1:
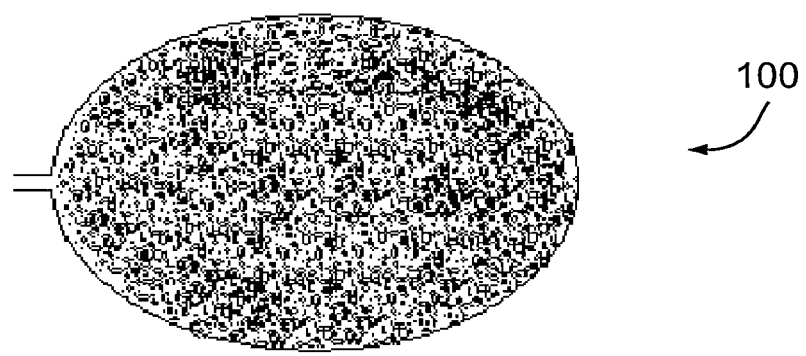
FIG. 1 is an illustration of a sponge-like expandable prosthesis adapted to reduce and/or eliminate injury to the rotator cuff, in accordance with an exemplary embodiment of the invention.

Referring to FIG. 1, an expandable prosthesis 100 is shown which is adapted to reduce and/or eliminate injury to the rotator cuff, in an exemplary embodiment of the invention. In an exemplary embodiment of the invention, expandable prosthesis 100 is introduced between the above mentioned acromion and coracoid processes and the rotator cuff tendons to prevent continued injury to these body parts and/or to permit relatively unhindered (relative to the movement afforded to the shoulder without treatment) or free shoulder movement, shown and described in more detail with respect to FIG. 3. In some embodiments of the invention, expandable prosthesis 100 comprises an expandable member which is a sponge-like structure. It should also be understood that sponge-like expandable prosthesis 100 is adapted to elute pharmacological substances such as anti-inflammatory and/or antibiotic and/or pro-angiogenesis substances, in some exemplary embodiments of the invention.

In an exemplary embodiment of the invention, sponge-like expandable prosthesis 100 is biodegradable and/or biocompatible. The sponge-like structure is manufactured from at least one biodegradable and/or biocompatible synthetic material such as, but not limited to, polycaprolactone ("PCL"), polyglycolide ("PGA"), polyhydroxybutyrate ("PHB"), plastarch material, polyetheretherketone ("PEEK"), zein, polylactic acid ("PLA"), polydioxanone ("PDO") and poly(lactic-co-glycolic acid) ("PLGA"), or any combination and/or family members thereof. In some exemplary embodiments of the invention, the sponge-like structure is manufactured from at least one "naturally-derived" biodegradable and/or biocompatible materials such as collagen and/or methyl cellulose. In an exemplary embodiment of the invention, sponge-like expandable prosthesis 100 is imparted expandable properties, at least in part, by placing within its cavities at least one biocompatible and/or biodegradable material which expands after coming into contact with fluids. Optionally, the fluids are bodily fluids. Optionally, the at least one biocompatible and/or biodegradable material is a gel.

In some exemplary embodiments of the invention, sponge-like expandable prosthesis 100 is non-biodegradable. Non-biodegradable expandable prostheses are manufactured of biocompatible materials such as polyethylene, Kevlar® (poly-paraphenylene terephthalamide), polyurethane or silicon, or any combination thereof, in some embodiments of the invention. In some exemplary embodiments of the invention, the expandable prosthesis is manufactured from biologically derived, biocompatible and/or biodegradable materials such as collagen. In an exemplary embodiment of the invention, prosthesis 100, when expanded, has approximately the same dimensions as other prostheses when expanded, described below.

Figure 2:
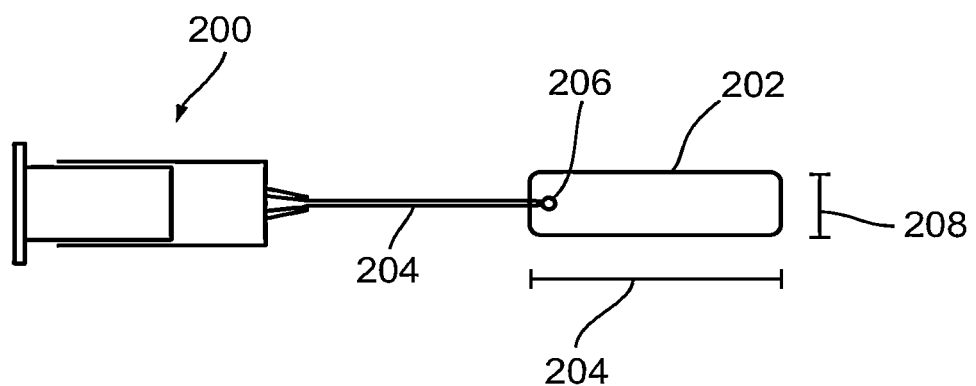
FIG. 2 is a cutaway view of a portion of a prosthesis implantation and/or inflation device and an inflatable expandable prosthesis adapted to reduce and/or eliminate injury to the rotator cuff, in accordance with an exemplary embodiment of the invention.

Referring to FIG. 2, a cutaway view of a portion of a prosthesis implantation and/or inflation device 200 and a prosthesis 202 with an expandable member which is inflatable is shown, in accordance with an exemplary embodiment of the invention. Exemplary embodiments of prosthesis implantation and/or inflation device 200 are described in more detail with respect to FIGS. 16-17. In an exemplary embodiment of the invention, inflatable expandable prosthesis 202 is introduced between the above mentioned acromion and coracoid processes and the rotator cuff tendons to prevent continued injury to these body parts and/or to permit relatively unhindered or free shoulder movement, shown and described in more detail with respect to FIG. 3. Optionally, alternatively and/or additionally, an expandable prosthesis comprises an inflatable structure and a sponge-like structure in combination.

In an exemplary embodiment of the invention, inflatable expandable prosthesis 202 is rectangular shaped when deflated and resembles a cuboid parallelepiped when inflated. In an exemplary embodiment of the invention, inflatable expandable prosthesis 202 is circular or oval in shape when deflated and when inflated resembles a cylindrical disc or ovoid. It should be understood, however, that many shapes could be adapted to be implanted between the acromion and coracoid processes and the rotator cuff tendons to prevent at least some injury to the rotator cuff and/or to permit relatively unhindered or free shoulder movement for a patient, in an exemplary embodiment of the invention. In some embodiments of the invention, prosthesis 202 is adapted to be inserted deflated into a patient's body through a cannula. Optionally, the cannula is a 5 mm-7 mm cannula. In an embodiment of the invention, a long axis 204 (x-axis) of inflatable expandable prosthesis 202 is approximately 2 cm to 10 cm in length when inflated. In some embodiments of the invention, a short axis 208 (y-axis) of inflatable expandable prosthesis 202 is approximately 2 cm to 7 cm in length when inflated In some exemplary embodiments of the invention, inflatable expandable prosthesis 202 is 0.5 mm to 20 mm in height (z-axis). Optionally, inflatable expandable prosthesis 202 is 1 mm to 10 mm in height. It should be understood that the deflated and/or inflated size of prosthesis 202 is adapted to fit for a patient's particular needs or to simulate the size and/or shape of the natural bursa, in an embodiment of the invention, and therefore, prosthesis 202 does not necessarily conform to the size ranges given above.

Inflatable expandable prosthesis 202 is manufactured by dip molding, in an exemplary embodiment of the invention. In some embodiments of the invention, inflatable expandable prosthesis 202 is a seamless balloon-like structure made from biocompatible and/or biodegradable synthetic materials such as, but not limited to, PCL, PGA, PHB, plastarch material, PEEK, zein, PLA, PDO and PLGA, or any combination and/or family members thereof. Additionally, optionally and/or alternatively, inflatable expandable prosthesis 202 is manufactured from natural, biocompatible and/or biodegradable materials such as collagen and/or methyl cellulose. In some exemplary embodiments of the invention, the inflatable prosthesis 202 is manufactured from at least one non-biodegradable material such polyethylene, polyurethane, silicon, and/or Kevlar®. In an embodiment of the invention, prosthesis 202 is comprised of a material which is approximately 100 microns in thickness, although, as with the other dimensions, the thickness dimension of the material is adapted depending on the intended use and/or the needs of the patient. In some exemplary embodiments of the invention, inflatable expandable prosthesis 202 is adapted to elute pharmaceuticals such as anti-inflammatory drugs and/or antibiotics and/or pro-angiogenesis factors to promote healing.

Inflatable expandable prosthesis 202 is releasably attached to prosthesis implantation and/or inflation device 200, in an exemplary embodiment of the invention. Prosthesis implantation and/or inflation device 200 is adapted to inflate and/or deflate prosthesis 202, allow prosthesis 202 to be positioned in vivo, and/or separate from prosthesis 202 after implantation, leaving prosthesis 202 at the implantation site, in an embodiment of the invention. In some exemplary embodiments of the invention, prosthesis implantation and/or inflation device 200 includes a tube or catheter type structure 204 which interfaces with prosthesis 202 in the proximity of a sealing mechanism 206 which is located at the end of tube 204 nearest prosthesis 202.

Figure 4A:
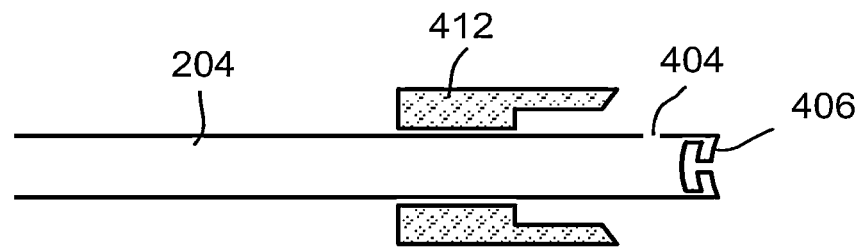
FIGS. 4A-C are cutaway side views showing the progression removably attaching a prosthesis implantation and/or inflation device and an expandable prosthesis, in accordance with an exemplary embodiment of the invention.
Figure 4B:
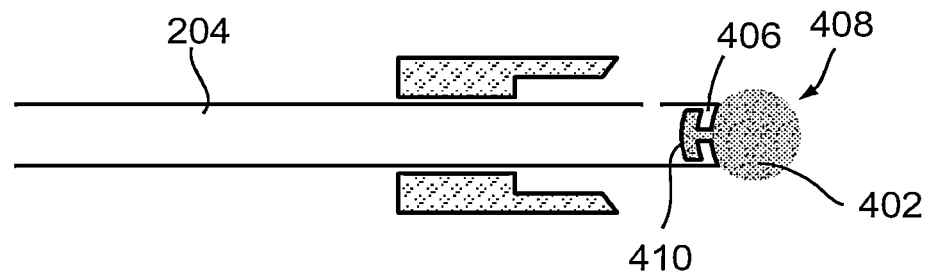

In an embodiment of the invention, sealing mechanism 206 includes a plug 402, shown in FIG. 4B inter alia, attached to the end of tube 204 nearest prosthesis 202. In an embodiment of the invention, plug 402 is constructed of the same material or materials as any of the prostheses described herein. Tube 204 is adapted to allow passage therethrough of the substance used to fill prosthesis 202, for example by placing at least one orifice 404 in tube 204. In some embodiments of the invention, air is used to inflate prosthesis 204. Additionally, alternatively and/or optionally, a biodegradable and/or biocompatible substance is used to inflate prosthesis 202. In some embodiments of the invention, a gel or liquid is used to inflate prosthesis 202. In an embodiment of the invention, tube 204 is provided with gripping protrusions 406 in order to increase the contact surface between tube 204 and plug 402 and therefore the force that may be applied to plug 402 when sealing prosthesis 202. In some embodiments of the invention, plug 402 is ovoid shaped, and/or has a shape such that plug's 402 loose end 408 is larger than the attached end 410 so that, as described in more detail below with respect to FIGS. 4A-C, 5 and 7, plug 402 seals inflatable expandable prosthesis 202 during implantation.

Figure 4C:
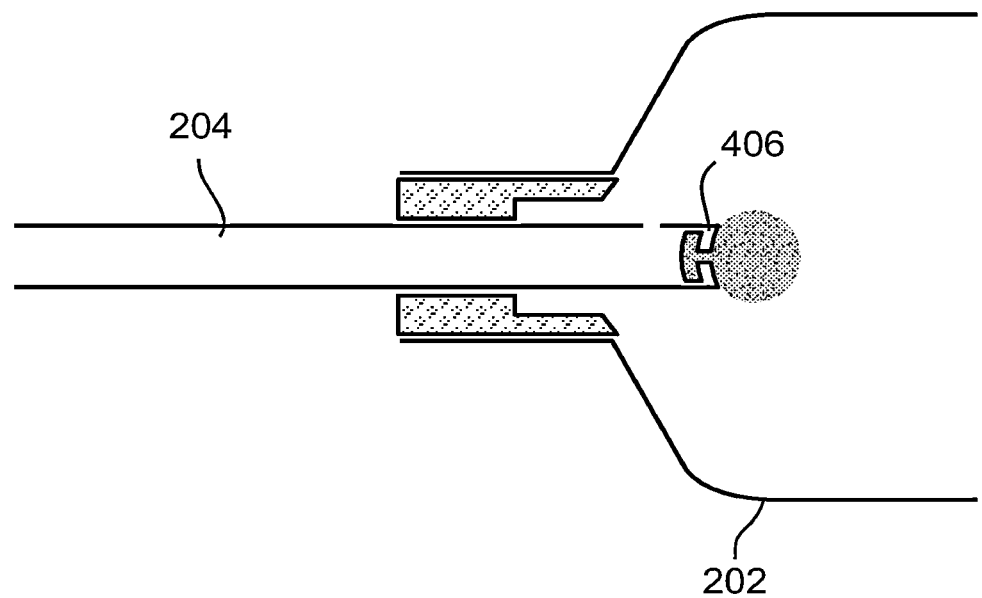

FIGS. 4A-C are cutaway side views showing the progression of removably attaching prosthesis implantation and/or inflation device 200 and prosthesis 202, in accordance with an exemplary embodiment of the invention. Referring to FIG. 4A, a rigid ring 412 is cast on tube 204 of prosthesis implantation and/or inflation device 200, in an embodiment of the invention. In an embodiment of the invention, rigid ring 412 fits snugly onto tube 204 such that air and/or other fluid injected into prosthesis 202 does not escape via the intersection of rigid ring 412 and tube 204, however tube 204 is slidable in relation to rigid ring 412. This slidability is useful, for example, when prosthesis implantation and/or inflation device 200 is separated from prosthesis 202 in accordance with an exemplary embodiment of the invention. In an exemplary embodiment of the invention, plug 402 is cast on tube 204 such that gripping protrusions 406 grasp at least a portion of attached end 410 of plug 402, shown in FIG. 4B. Optionally, dip molding, or any other method known in the art, is used for manufacturing plug. At least tube 204 and/or plug 402 and/or rigid ring 412 are made of biodegradable and/or biocompatible materials, in an embodiment of the invention.

Rigid ring 412 is cast on tube 204 before plug 402 is cast tube 204 because in an exemplary embodiment of the invention, plug 402 has a larger diameter than the inner diameter of rigid ring 412 thereby preventing plug 402 from passing through rigid ring 412. In an embodiment of the invention, inflatable expandable prosthesis 202 is placed around plug 402 and tube 204 such that tube 204 and plug 402 extend into a cavity proscribed by prosthesis 202. Prosthesis 202 is attached to an exterior surface of rigid ring 412 such that air and/or other fluid injected into prosthesis 202 does not escape via the intersection of prosthesis 202 and rigid ring 412, in an embodiment of the invention. Optionally, a thermal method is used to attach prosthesis 202 to rigid ring 412.

Figure 5:
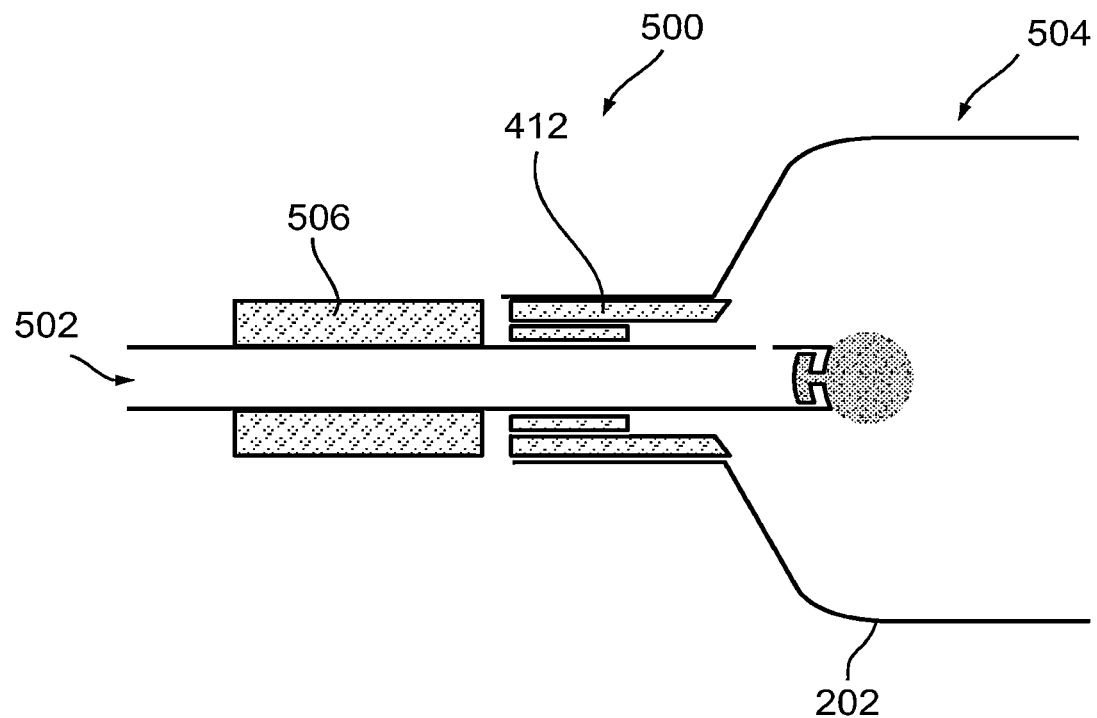
FIG. 5 is a cutaway side view of a portion of a prosthesis implantation and/or inflation device including a counter-pressure sheath and an expandable prosthesis, in accordance with an exemplary embodiment of the invention.

FIG. 5 shows an assembly 500 including a portion 502 of inflation device 200 and a portion 504 of expandable prosthesis 202 further comprising a counterforce ring 506, in accordance with an exemplary embodiment of the invention. In an embodiment of the invention, counterforce ring 506 is adapted to apply counterforce to rigid ring 412 during separation of prosthesis inflation device 200 from prosthesis 202, as described in more detail below with respect to FIG. 7. In some embodiments of the invention, counterforce ring 506 is constructed of a biocompatible material, for example stainless steel and/or plastic, that is approximately at least as hard as rigid ring 412.

Figure 6:
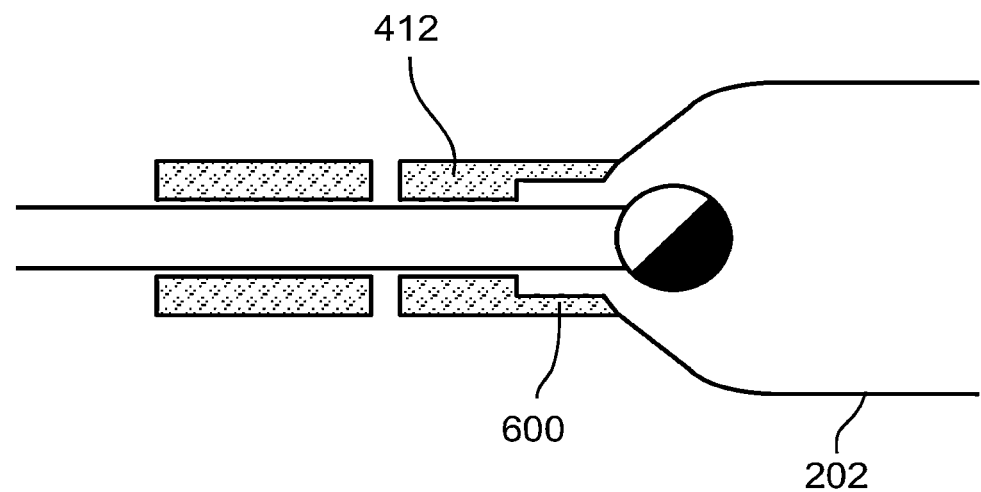
FIG. 6 is a cutaway side view of an alternative sealing mechanism, in accordance with an exemplary embodiment of the invention.

In some embodiments of the invention, at least one unidirectional valve 600, shown in FIG. 6, is used in addition to or alternatively to plug 402 and rigid ring 412 for sealing prosthesis 202 after at least partially inflating prosthesis 202 with prosthesis implantation and/or inflation device 200.

Figure 3:
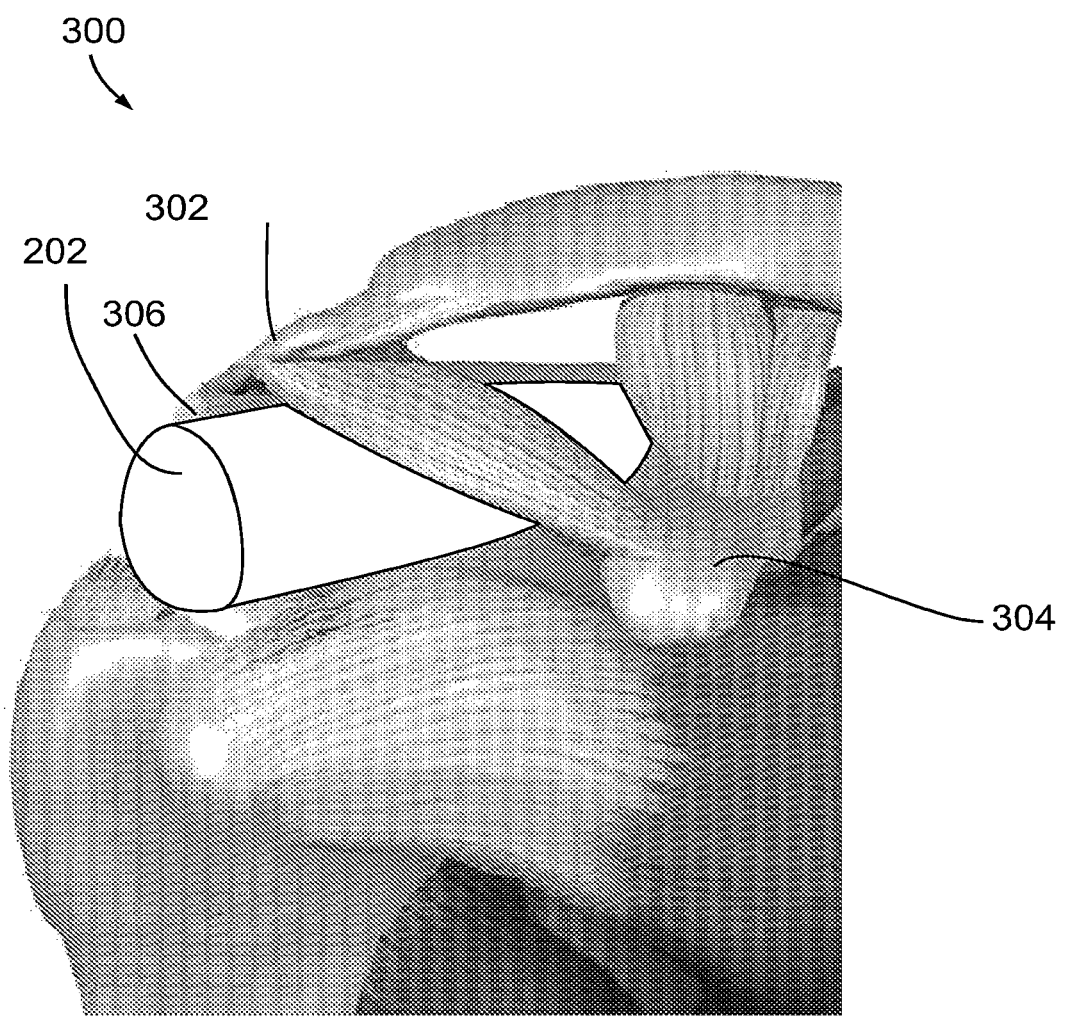
FIG. 3 is an anatomical view of a human shoulder with an expandable prosthesis in vivo, in accordance with an exemplary embodiment of the invention.

FIG. 3 shows an anatomical view of a human shoulder 300 with an expandable prosthesis 100, 202 in vivo, in accordance with an exemplary embodiment of the invention. Prosthesis 100, 202 is inserted between the acromion 302 and the coracoid process 304, in an embodiment of the invention. In some embodiments of the invention, prosthesis 100, 202 and any other prosthesis described herein, is inserted proximal to the bursa 306. Optionally, if there is no bursa 306 of any remarkable size, the prosthesis is inserted in lieu of bursa 306. In an embodiment of the invention, an implanted prosthesis, such as those described herein, is adapted to cover the humerus head during shoulder 300 motion, while remaining relatively fixed in relation to the acromion 302 and/or the coracoid process 304.

In some embodiments of the invention, an anchoring expandable prosthesis is adapted to prevent and/or reduce injury to the rotator cuff and/or to permit relatively unhindered or free shoulder movement. The anchoring expandable prosthesis comprises an expandable member and at least one anchoring device which is adapted to be attached to a part of the patient, for example the humerus head/tendons, acromion and/or coracoid process, thereby anchoring the prosthesis in place. In an embodiment of the invention, the anchoring expandable prosthesis comprises at least one anchoring device attached to an expandable portion adapted to operate similarly to prostheses 100, 202. The at least one anchoring device is manufactured of biocompatible and/or biodegradable or non-biodegradable metals and/or alloys and/or composites, for example titanium, stainless steel or magnesium alloys. In an embodiment of the invention, the expandable portion is manufactured of biocompatible and/or biodegradable or non-biodegradable materials such as high density polyethylene or those described with respect to prostheses 100, 202. In an embodiment of the invention, the at least one anchoring device is attached to the expandable member using filaments and/or wires.

In some embodiments of the invention, prostheses described herein are adapted for anchoring, for example by contouring the outer surface such that surrounding tissues can be placed within the contours, thereby "anchoring" the device. In some embodiments of the invention, the contours are adapted to act as counterparts to anatomical features at the implantation site, whereby the features settle into the contours upon implantation, but still permit relatively unhindered movement of the treated area.

Prostheses 100, 202, and/or any of the other prostheses described herein, are adapted for use in places where there is sliding of soft tissues, such as tendons against other tissues, such as bones as: a) between the quadriceps and femur after operations on the knee, b) near the finger flexor and/or extensor to prevent adhesions, for treatment of ailments such as carpal tunnel syndrome or, c) between the skin and plantar fascia and calcaneus in case of calcaneal spur, in some exemplary embodiments of the invention. As described above, the prosthesis used for treatment of particular ailments is sized and/or shaped to simulate the natural bursa found at the location being treated, in an exemplary embodiment of the invention.

In an embodiment of the invention, an expandable prosthesis which is least slightly elastic, but not inflatable, is adapted to prevent and/or reduce injury to the rotator cuff and/or to permit relatively unhindered or free shoulder movement. In some embodiments of the invention, the elastic prosthesis is manufactured from polyethylene and/or silicon and/or in combination with metals, such as titanium. Optionally, the elastic prosthesis is contoured to serve as a counterpart to the surfaces with which it will come into contact. For example in the case of a rotator cuff, the elastic prosthesis may be contoured to fit at least the acromion.

In an embodiment of the invention, a prosthesis is provided which is substantially rigid. The rigid prosthesis is constructed of a biocompatible material, for example stainless steel and/or a hard plastic, in some embodiments of the invention. Optionally, the rigid prosthesis is also biodegradable. In some embodiments of the invention, the rigid prosthesis is adapted to act as a counterpart to at least one anatomical feature at the implantation site, whereby the feature mates with the rigid prosthesis upon implantation, but still permits relatively unhindered movement of the treated area. As an example, the rigid prosthesis is adapted to mate with both the humerus head and the acromion upon implantation, in an embodiment of the invention.

Figure 7:
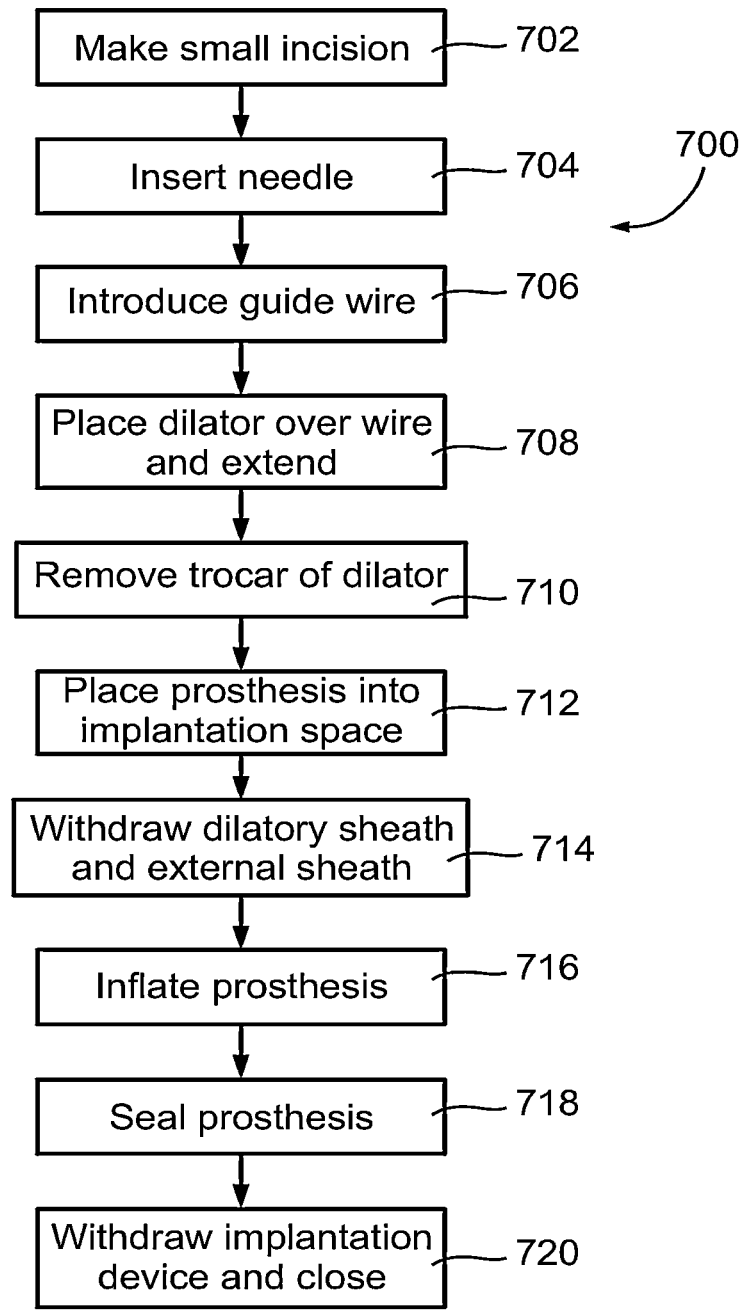
FIG. 7 is a flowchart demonstrating a method of implanting an expandable prosthesis, in some exemplary embodiments of the invention.

Referring to FIG. 7, a method 700 of implanting an expandable prosthesis 100, 202, or any other prosthesis described herein is described, in some exemplary embodiments of the invention. In an embodiment of the invention, implantation method 700 is adapted for implantation of prostheses 100, 202, or any other prosthesis described herein, into the shoulder of a patient to prevent and/or reduce injury to the rotator cuff and/or to permit relatively unhindered or free shoulder movement. In an embodiment of the invention, prostheses 100, 202, or any other prosthesis described herein, are introduced percutaneously or by making (702) a small incision, optionally performed by posterior, lateral or anterior approaches using, for example, palpation, arthroscopy, ultrasound ("US"), computed tomography ("CT"), magnetic resonance imaging ("MRI"), fluoroscopy, transmission scan ("TX"), or any combination thereof. In an embodiment of the invention, a needle is inserted (704) into the space between the rotator cuff tendons and the acromion 302 and coracoid process 304. A guide wire is introduced (706) via the needle into the space between the rotator cuff tendons and the acromion 302 and coracoid process 304, in an exemplary embodiment of the invention. In some embodiments of the invention, a dilator is placed (708) over the guide wire and extended into the space. Subsequently, a trocar of the dilator is removed (710), leaving a dilator sheath in place.

Figure 8:
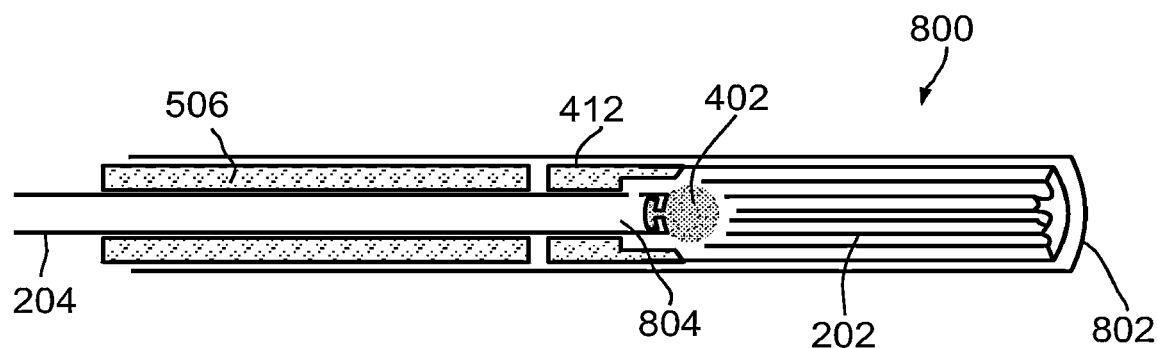
FIG. 8 is a cutaway side view of an expandable prosthesis packed prior to use, in accordance with an exemplary embodiment of the invention.

In an embodiment of the invention, inflatable expandable prosthesis 202 is placed (712) into the space using the dilator sheath and/or the prosthesis inflation device 200 for guidance and/or movement impetus. Once prosthesis 202 is approximately in the proper position, the dilator sheath and an external sheath 802 of prosthesis inflation device 200, shown and described in more detail with respect to FIG. 8, are withdrawn (714) to allow for inflation (716) of prosthesis 202. Inflation (716) using prosthesis inflation device 200 is described in more detail below. Inflation (716) of prosthesis 202 is achieved, in some embodiments of the invention, during arthroscopy. In some embodiments of the invention, for example if prosthesis 202 is implanted during open surgery or arthroscopy, proper deployment of prosthesis 202 is ascertained by visual inspection of prosthesis 202. In an embodiment using arthroscopy, prosthesis may be introduced through an arthroscopy port. In some embodiments of the invention, inflation (716) is achieved using palpation and US guidance to ascertain proper deployment of prosthesis 202. In some embodiments of the invention, inflation (716) is achieved using fluoroscopy to ascertain proper deployment of prosthesis 202. Proper deployment of prostheses, in some embodiments of the invention, means no interposition of tendons and/or other soft tissue between the implanted prosthesis and acromion 302 or coracoid process 304 and/or that during movement of the humerus, the prosthesis remains below acromion 302.

Inflation (716) of prosthesis 202 is performed using prosthesis inflation device 200, in an embodiment of the invention. It should be understood that only a portion of prosthesis inflation device 200 is shown in FIG. 2, and that exemplary variations are shown in more detail with respect to FIGS. 16-17. Referring to FIG. 8, an expandable prosthesis 202 is shown packed for implantation and prior to deployment, in accordance with an exemplary embodiment of the invention. Components of the assembly 800 are enclosed in an external sheath 802 which surrounds at least prosthesis 202, in an exemplary embodiment of the invention. External sheath 802 is adapted to maintain prosthesis 202 in a collapsed condition during placing (712) in order to ease insertion of prosthesis 202 into the implantation space or site through the dilator sheath, in an embodiment of the invention. As described above, once prosthesis 202 is in the implantation space, external sheath 802 is removed, enabling prosthesis 202 to be inflated without hindrance apart from the body parts against which prosthesis 202 is pressing.

In an embodiment of the invention, inflation (716) of prosthesis 202 is performed using a physiologic fluid such as saline, Hartman or Ringer solutions and/or any other biocompatible and/or biodegradable fluid. In some embodiments of the invention, inflation (716) is performed using a biocompatible and/or biodegradable gel. In an embodiment of the invention, inflation (716) of prosthesis 202 is performed using a gas, for example air and/or carbon dioxide. In some embodiments of the invention, the inflating gel and/or fluid contains pharmaceutical agents, for example anti-inflammatory drugs and/or antibiotics and/or pro-angiogenesis factors to promote healing, which are eluted into the patient's body. In some embodiments of the invention, prosthesis 202 is inflated to the maximum volume possible without reducing the shoulder's range of movement. In an embodiment of the invention, prosthesis 202 is filled to less than its maximum volume in order to permit shifting of the contents of prosthesis 202 during movement. Optionally, prosthesis 202 is filled to 60%-70% of its maximum volume (for example, an expandable member with a 14 cc volume is filled with 9 cc of filler). It should be noted that other prosthesis embodiments described herein are deployed in a similar fashion, in some embodiments of the invention.

Sealing (718) of prosthesis 202, once inflated to the desired level, is performed by pulling tube 204 towards rigid ring 412 as they slide in relation to one another plug 402 becomes lodged in a lumen 804 of rigid ring 412 and continued pulling brings rigid ring 412 into contact with counterforce ring 506, in an embodiment of the invention. In an embodiment of the invention, tube 204 passes through lumen 804 with lumen 804 providing fluid communication between prosthesis implantation and/or inflation device 200 and an inner space defined by the dimensions of prosthesis 202. In an embodiment of the invention, an attending medical professional performing the implantation procedure holds counterforce ring 506 substantially steady while pulling on tube 204 away from the patient. Optionally, prosthesis inflation device 200 is adapted to perform the steadying of counterforce ring 506 and/or retraction of tube 204 automatically. In some embodiments of the invention, a mechanism is provided to prosthesis inflation device 200 which translates rotational movement to a retracting force on tube 204. Optionally, rotation movement is applied manually.

Continued pulling ("retraction" away from patient) of tube 204 causes a portion of plug 402 to break off, the portion of plug 402 lodging itself in lumen 804 of rigid ring 412 thereby sealing prosthesis 202. In some embodiments of the invention, the portion of plug 402 becomes partially deformed as it lodges in lumen 804. Prosthesis inflation device 200, now being separated from prosthesis 202 as a result of sealing (718) is withdrawn (720) from the patient and patient is closed, in an exemplary embodiment of the invention. It should be understood that in some embodiments of the invention, a sponge-like expandable prosthesis device is used and therefore, inflation (716) and inflation related actions may not be carried out, for example prosthesis 100 expands rather than inflates.

In an exemplary embodiment of the invention, the implanted prosthesis is secured, using methods known in the art, to soft tissue and/or bone to prevent the prosthesis from being easily displaced by shoulder movement. In some embodiments of the invention, sutures, clips and/or anchors are used to secure the prosthesis in place. Optionally, an anchoring expandable prosthesis is used. In an embodiment of the invention, simulating a naturally occurring bursa using a prosthesis is an action taken with respect to method 700. Optionally, simulating is related to inflation (716) in that the prosthesis is inflated to resemble the appropriate size and/or shape and/or characteristics (malleability, compressibility, etc.) of the naturally occurring bursa. In an embodiment of the invention, placing the prosthesis at the implantation site and simulating a naturally occurring bursa does not significantly reduce movement of the soft tissues being protected in relation to the other tissues at the implantation site.

In an exemplary embodiment of the invention, prosthesis 100 is implanted by placing prosthesis 100 into a cannula, such as those described elsewhere herein, and advancing it to the implantation site using a plunger.

In an exemplary embodiment of the invention, prosthesis 100 or the elastic prosthesis, described above, is implanted by inserting the device directly through a small incision, without a cannula, near the implantation site.

It should be noted that the method shown and described with respect to FIG. 7 is by way of example only, and that similar methods could be used for implantation of any bursa simulating prosthesis adapted for reducing injuries between soft tissues and other tissues of the body.

Figure 9:
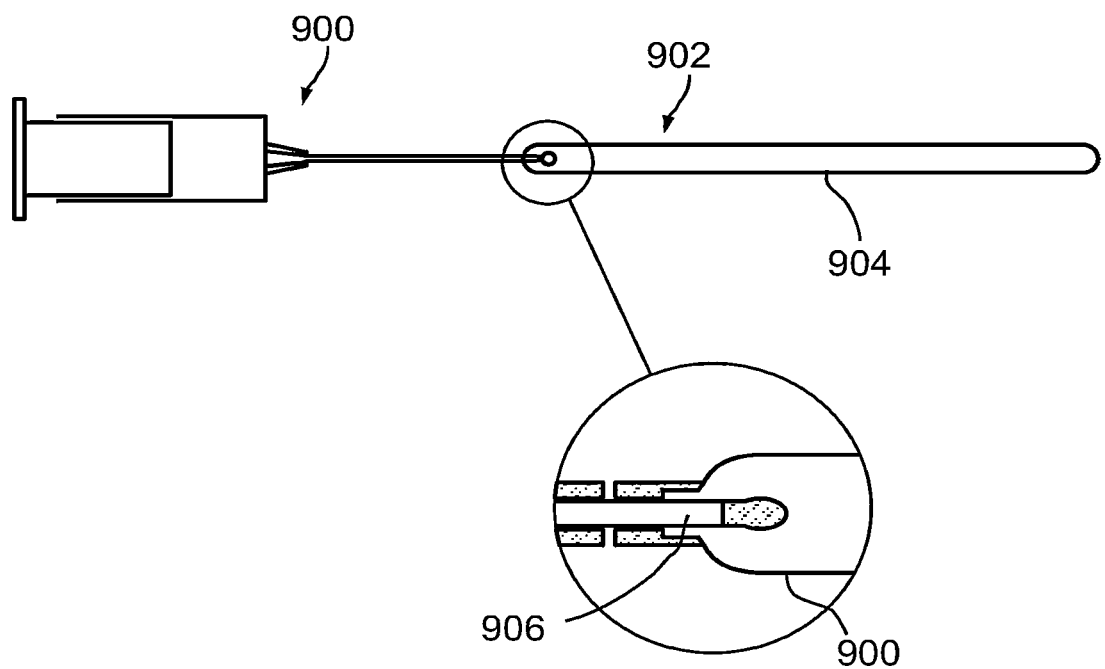
FIG. 9 is a cutaway side view of a portion of a prosthesis implantation and/or inflation device and an expandable prosthesis for alignment of bone fragments, in accordance with an exemplary embodiment of the invention.

Referring to FIG. 9, a cutaway side view of a portion of a prosthesis implantation and/or inflation device 900 and an expandable prosthesis 902 for alignment of bone fragments in the case of fractures of tubular bones is shown, in accordance with an exemplary embodiment of the invention. Prosthesis 902 is adapted to fit in the medullar cavity of the bone in which it is intended to be used and is optionally biodegradable and/or biocompatible. In an embodiment of the invention, prosthesis 902 is intended to be used in non-weight bearing bones, for example, the humerus, radius, and ulna. Prosthesis 902 comprises an inflatable tubular member 904 which is generally shaped to fit within a medullar cavity of the bones to be aligned. Optionally, inflatable tubular member 904 is tubular or vasiform. Optionally, inflatable tubular member 904 is slightly curved. In an embodiment of the invention, inflatable tubular member 904 has an approximate outer diameter ranging between 2 to 15 mm and having an approximate length ranging between 5 to 50 cm. Optionally, the outer diameter ranges between 4 to 10 mm. Optionally, the length ranges between 10 and 30 cm. In an embodiment of the invention, prosthesis 902 is sized and/or shaped to fit into the medullar cavities of the bone fragments which are intended to be aligned.

Prosthesis 902 is releasably attached to prosthesis implantation and/or inflation device 900 and/or inflated in a similar fashion as described with respect to prosthesis 202 and implantation and/or inflation device 200, in an embodiment of the invention.

At least part of prosthesis 902 (e.g. tubular member 904) is manufactured, in an embodiment of the invention, by dip molding. Optionally, inflatable tubular member 904 is a seamless balloon made from biocompatible and/or biodegradable synthetic materials such as, but not limited to, PLA, PLGA, PCL, PDO, or any combination and/or families thereof. In an embodiment of the invention, inflatable tubular member 904 is provided with an outer wall thickness adapted to accommodate at least a minimum level of rigidity necessary to maintain the aligned bone fragments during normal activity. For example, forearm bones are normally subjected to forces ranging from a few hundred grams to several kilograms during normal activity. As another example, metacarpal bones are normally subjected to tens of grams to a few hundred grams of force. It should be noted that these ranges are provided as examples only and that depending on patient and/or the bone fragments being aligned, the wall thickness of inflatable tubular member will be adapted to maintain alignment of the bone fragments in spite of the anticipated stress on prosthesis 902 during normal activity and/or rehabilitation of the patient.

In an exemplary embodiment of the invention, inflation of prosthesis 902 is performed using a physiologic fluid such as saline, Hartman or Ringer solutions and/or any other biocompatible and/or biodegradable fluid. In some embodiments of the invention, inflation is performed using a biocompatible and/or biodegradable gel. In an embodiment of the invention, inflation of prosthesis 902 is performed using a gas, for example air and/or carbon dioxide. In an embodiment of the invention, prosthesis 902 is filled with a cement that hardens and/or seals the open end 906 of prosthesis 902. In some embodiments of the invention, the cement is used provide alignment for the fractured bone segments.

In an exemplary embodiment of the invention, prosthesis 902 is adapted to elute at least one pharmaceutical agent, for example anti-inflammatory drugs and/or antibiotics and/or bone deposition promoting factors and/or pro-angiogenesis factors to promote healing of the fracture.

In some embodiments of the invention, prosthesis 902 (and/or other prostheses described herein) is used with a calibration kit which determines the size of the medullar cavity and/or the proper size inflatable tubular member 904 to use with the medullar cavity. Optionally, the calibration kit is integrated with prosthesis 902. Optionally, the calibration kit is integrated with prosthesis implantation and/or inflation device 900. In an embodiment of the invention, a calibration expandable member is first deployed into the medullar cavity to measure the cavity shape and/or size and then upon deployment of prosthesis 902, its shape and/or size is adapted to match the needs of the measured medullar cavity. Optionally, various sizes of dilators are used in conjunction with the calibration expandable member to assist with determining size.

Figure 10:
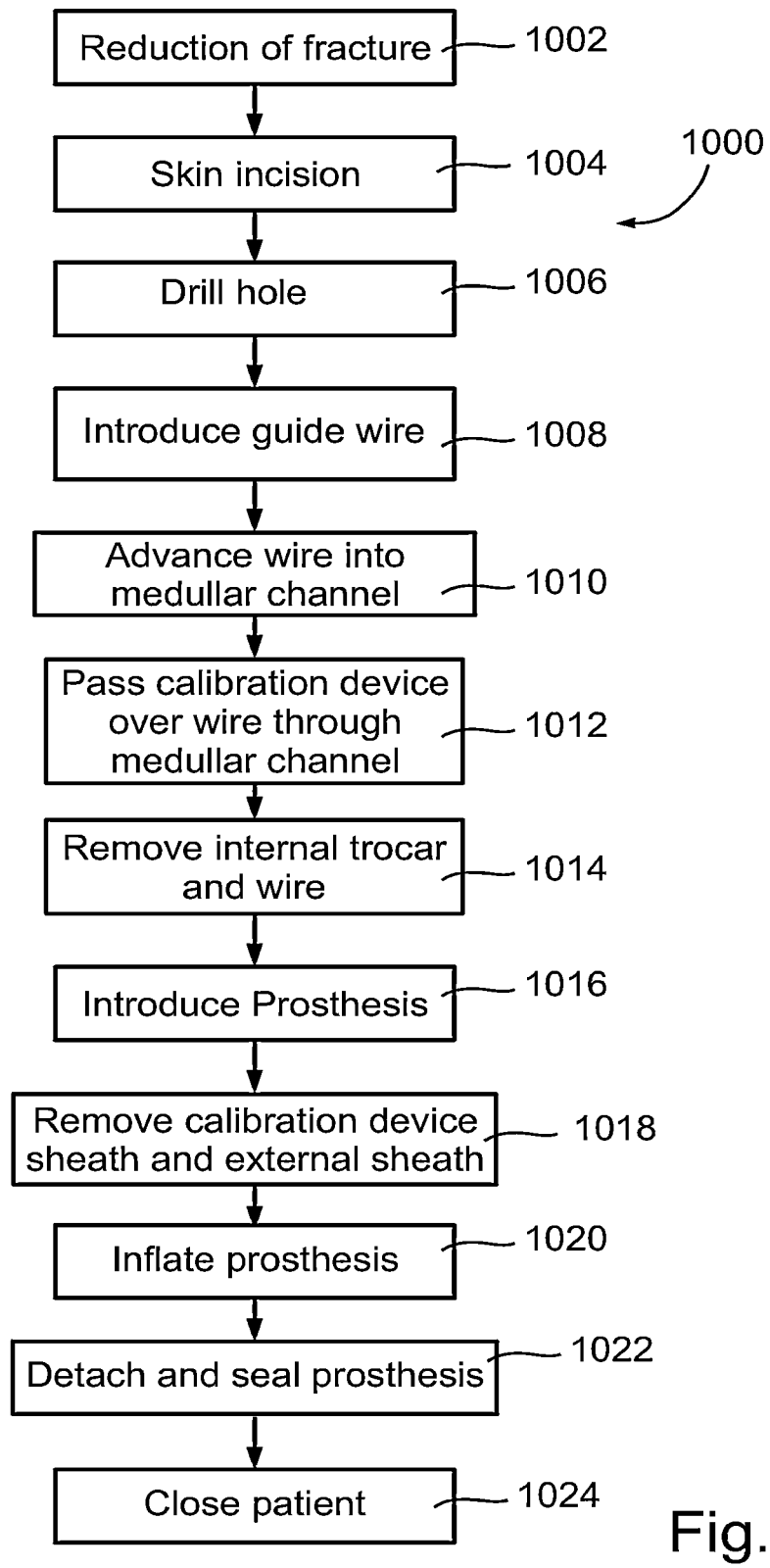
FIG. 10 is a flowchart showing a method of aligning two or more segments of bone, in accordance with an exemplary embodiment of the invention.

FIG. 10 is a flowchart 1000 showing a method of aligning two or more segments of bone, in accordance with an exemplary embodiment of the invention. Reduction (1002) of the fracture is performed, in an exemplary embodiment of the invention, by closed reduction. The closed reduction maneuvers are performed under fluoroscopic and/or TX guidance, in some embodiments of the invention. A skin incision is performed (1004) over a first segment of bone. In an embodiment of the invention, a hole is drilled (1006) through the compact bone of one of the bone segments near the epiphyseal plate into the medullar channel and a guide wire is introduced (1008) through this medullar channel and advanced (1010) into the medullar channel of the other segment of bone passing through the fracture site. When more than two fragments of bone exist, in an embodiment of the invention, the wire passes through the medullar channels of all segments.

A calibration device comprising a sheath and an internal trocar is passed (1012) over the wire through the medullar channels of the bone segments, in an embodiment of the invention. The internal trocar and the wire are removed (1014) leaving inside only the external sheath of the calibration device within the medullar channel of the bone segments, in an exemplary embodiment of the invention. Prosthesis 902 is introduced (1016) into this sheath, in an embodiment of the invention. The calibration device sheath and the external sheath of prosthesis 902 (similar in form and function to external sheath 802) are removed (1018) in an embodiment of the invention and the unexpanded prosthesis 902 remains in the medullar channels of the segments of bone.

Figure 11:
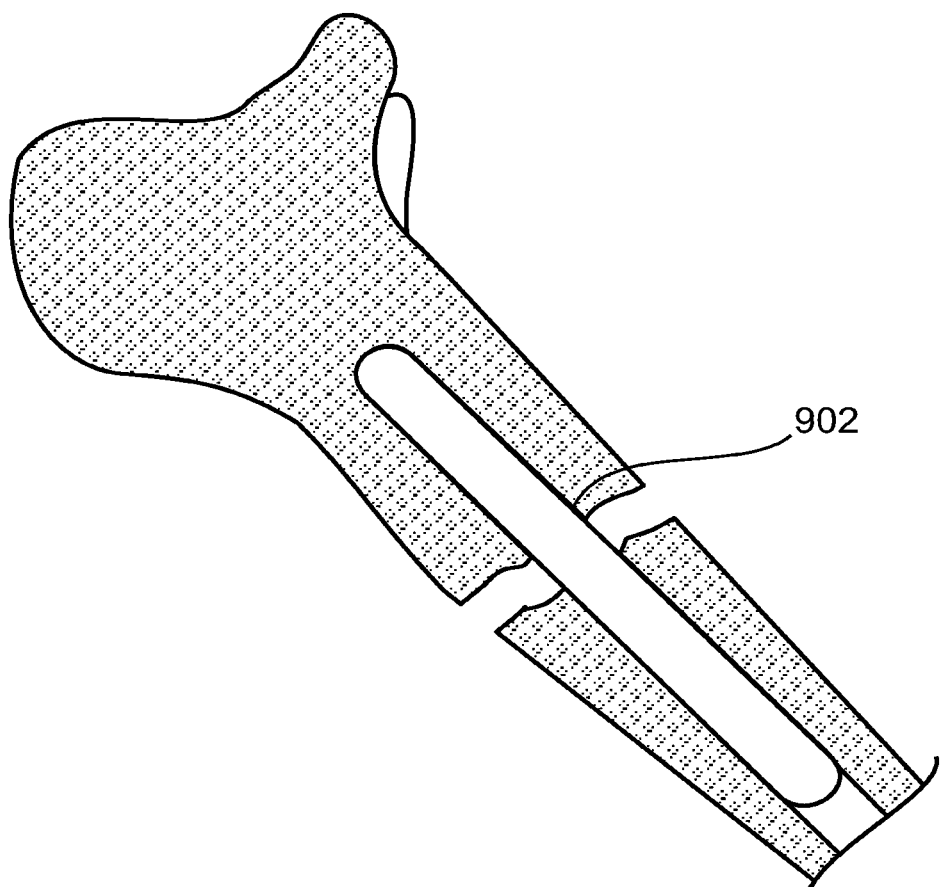
FIG. 11 is a cutaway side view of an expandable prosthesis for aligning bone fragments in vivo, in accordance with an exemplary embodiment of the invention.

In an embodiment of the invention, prosthesis 902 is inflated (1020) as described above with a biocompatible and/or biodegradable filler and the prosthesis 902 is detached (1022) sealing prosthesis 902 under pressure. The sealing is performed using any of the previously described methods or by any method known to those skilled in the art. In an embodiment of the invention, prosthesis 902 remains within the reduced bone segments keeping them in alignment, as shown in FIG. 11. The skin incision is closed (1024). In some embodiments of the invention, healing of the bone fragments is accelerated by eluting pharmaceutical agents from prosthesis 902.

In an embodiment of the invention, alignment of the bone segments is maintained by the rigidity of prosthesis 902. In an embodiment of the invention, the rigidity of prosthesis 902 at least partly depends on the internal pressure of prosthesis 902, the internal pressure being at least partly determined by the filler used and/or the percentage of prosthesis 902 that is filled by the filler. Optionally, an external cast is placed on the area proximal to the fracture.

Figure 12:
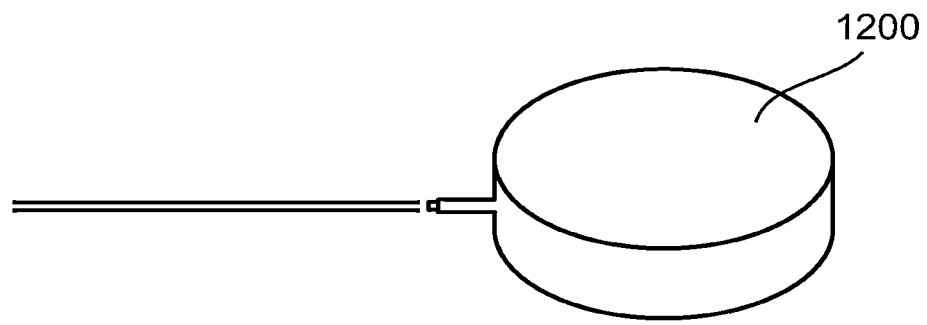
FIG. 12 is a perspective view of a device for treating inflammation and/or infection, in accordance with an exemplary embodiment of the invention.

FIG. 12 is a perspective view of a device 1200 for treating inflammation and/or infection, in accordance with an exemplary embodiment of the invention. In an embodiment of the invention, device 1200 is a sponge-like structure. In some embodiments of the invention, device 1200 is an inflatable structure. Device 1200 is adapted to be placed at a site in the body for treating inflammation and/or infection, in an embodiment of the invention, in an embodiment of the invention.

In an exemplary embodiment of the invention, a sponge-like device 1200 is manufactured of biocompatible and/or biodegradable synthetic materials such as, but not limited to, PLA, PLGA, PCL, PDO, or any combination thereof. Alternatively and/or additionally and/or optionally, it may be manufactured from biologically derived biodegradable materials such as collagen. Expandable sponge-like device 1200 optionally contains within its cavities at least one biocompatible and/or biodegradable gelling material, such as methyl cellulose, agarose, poly(ethylene-glycol) ("PEG") gel and/or PLA gel, that expands when it comes into contact with at least one bodily fluid, for example by absorbing water. In an embodiment of the invention, such absorption is partly responsible for an expansion of sponge-like device 1200 into its intended deployed position.

As described above, in some exemplary embodiments of the invention, device 1200 comprises an inflatable structure. In an embodiment of the invention, inflatable device 1200 is constructed of at least one biocompatible and/or biodegradable material, such as those described herein. In some embodiments of the invention, inflatable device 1200 is spherical or cylindrical, having a diameter of 0.5 cm to 5 cm for a sphere or in the long direction (x-axis) and 0.5 cm to 4 cm in the short direction (y-axis) and a height (z-axis) of 0.5 mm to 20 mm. In some embodiments of the invention, device 1200 is adapted to be inserted deflated into a patient's body through a cannula. Optionally, the cannula is a 5 mm-7 mm cannula. Optionally, device 1200 dimensions are adapted for a particular intended use.

In some exemplary embodiments, device 1200 is inflated and/or implanted as described herein with respect to prostheses 100, 202, 902. Device 1200 optionally contains pharmaceutical agents, for example anti-inflammatory drugs and/or antibiotics and/or pro-angiogenesis factors to promote healing, which are eluted into the body. In some embodiments of the invention, device 1200 is adapted to elute pharmaceutical agents according to a predefined schedule. Adaptation of device 1200 includes construction of device 1200 using materials or combinations of materials which degrade at a predetermined rate, thereby releasing pharmaceutical agents contained therein at a predetermined rate. In an exemplary embodiment of the invention, more than one device 1200 is used for treating inflammation and/or infection. Optionally, each device is adapted to elute pharmaceutical agents in view of an overall plan incorporating a plurality of devices.

In another exemplary embodiment of the invention, an expandable device, such as those described herein, is adapted to be used near an articulation to reinforce the articular capsule. In an embodiment of the invention, the expandable device is introduced in anterior fashion to the shoulder articulation between the articular capsule and the deltoid and pectoralis muscle, in order to prevent recurrent dislocation of the shoulder. In another embodiment, the expandable device is introduced in front of the hip joint capsule to prevent anterior dislocation of the hip, especially in cases of congenital dysplasia of hip. In an exemplary embodiment of the invention, the expandable device consists of in inflatable member made of biocompatible and/or biodegradable material. In some embodiments of the invention, the expandable device has a diameter of 1 cm to 7 cm in the long direction (x-axis) and 1 cm to 5 cm in the short direction (y-axis) with a height (z-axis) of 0.5 mm to 25 mm. Optionally, the device has a height of 3 mm to 15 mm.

Figure 13:
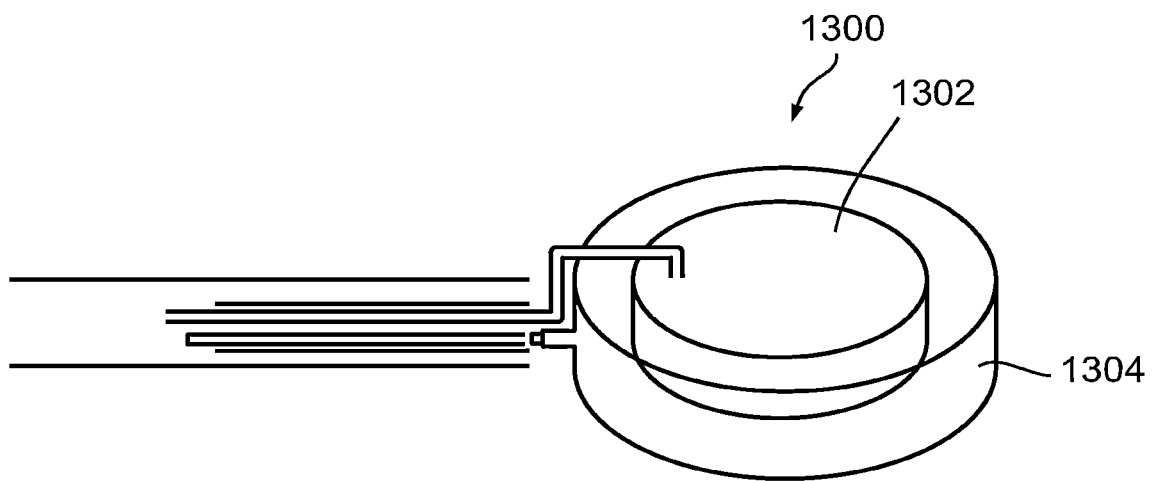
FIG. 13 is a perspective view of a device for treating depressed fractures, in accordance with an exemplary embodiment of the invention.

FIG. 13 shows a perspective view of a device 1300 for treating depressed fractures, for example osteoporotic fractures of the vertebra, in accordance with an exemplary embodiment of the invention. In some exemplary embodiments of the invention, device 1300 comprises at least two separately expandable sections, an inner section 1302 and an outer section 1304. In an embodiment of the invention, at least one expandable section is inflatable. In some embodiments of the invention, inner section 1302 when inflated takes a cylindrical shape measuring approximately 2 to 7 cm in diameter and 2 to 5 cm in height. Optionally, inner section 1302 is larger or smaller depending on the intended use of device 1300 and/or the particular needs of the patient Inner section 1302 is manufactured from materials such as polyurethane, ultra high molecular weight polyethylene ("Spectra®") and/or Kevlar® and/or any reinforced material that can withstand expected pressures on device 1300 as a result of the intended use, in an embodiment of the invention. In some embodiments of the invention, inner section 1302 is manufactured from a biocompatible and/or biodegradable substance such as PCL, PGA, PHB, plastarch material, PEEK, zein, PLA, PDO and PLGA, collagen, methyl cellulose, or any combination and/or family members thereof.

Expandable outer section 1304 at least partially surrounds inner section 1302, in an exemplary embodiment of the invention. In some embodiments of the invention, external section is a sponge-like structure, for example like other sponge-like structures described herein. Optionally, outer section 1304 is an inflatable structure, for example like other inflatable structures described herein. In some exemplary embodiments of the invention, outer section 1304 resembles a hollow cylinder, wheel and/or torus. In some embodiments of the invention, outer section 1304 is made of a biocompatible and/or biodegradable material, such as those described herein and known to those in the art.

In an embodiment of the invention, inner section 1302 and outer section 1304 are operatively connected to separate inflation devices. Optionally, only one inflation device is needed, for example if outer section 1304 or internal section 1302 is a sponge-like structure. In some exemplary embodiments of the invention, components of device 1300 are removably attached to at least one inflation device such as described elsewhere herein.

Figure 14:
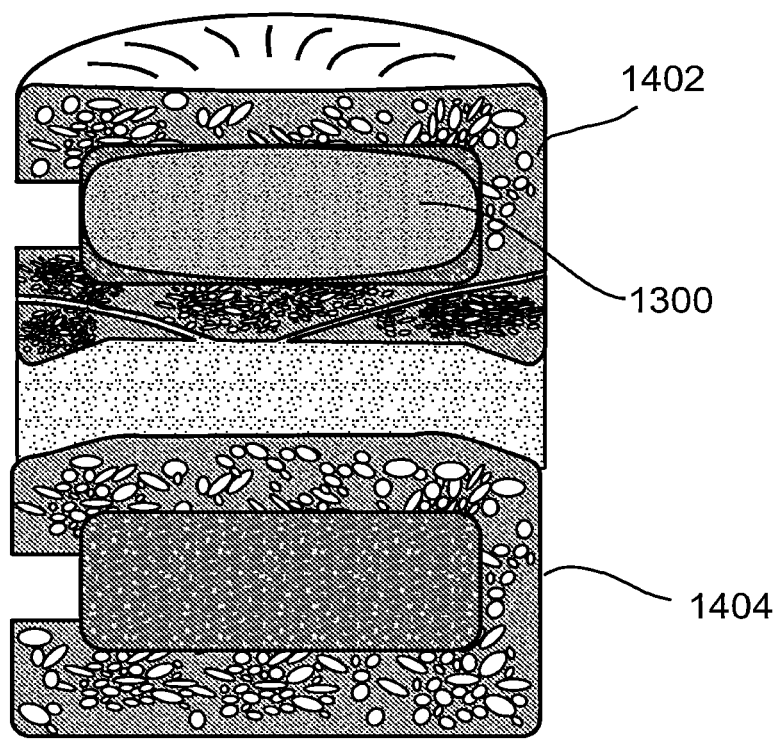
FIG. 14 is a perspective view, with a cutaway side view of two vertebrae, of a device for treating depressed fractures of vertebrae, in accordance with an embodiment of the invention.

FIG. 14 is a perspective view, with a cutaway side view of two vertebrae 1402, 1404, of a device 1300 for treating depressed fractures of a vertebra in vivo, in accordance with an embodiment of the invention. In some embodiments of the invention, device 1300 is adapted to treat osteoporotic fractures of vertebrae. As described below, device 1300 is used to deploy a filler, for example cement, to act as a force for restoring the natural shape of the fractured vertebra, thereby relieving pain and restoring at least a modicum of function to the patient.

Figure 15:
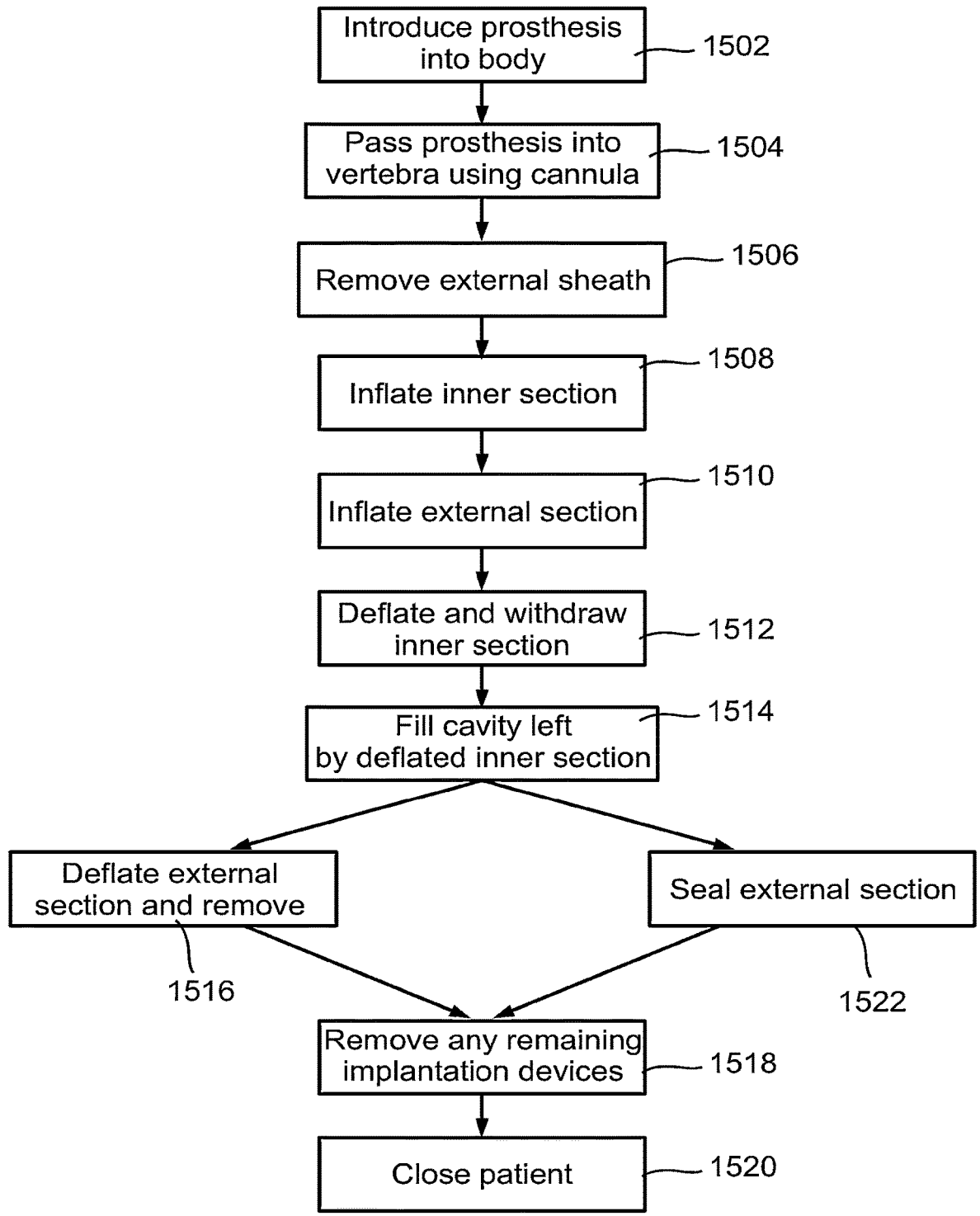
FIG. 15 is a flowchart showing a method of treating depressed fractures, in accordance with an exemplary embodiment of the invention.

FIG. 15 is a flowchart 1500 showing a method of treating depressed fractures, in accordance with an exemplary embodiment of the invention. In an exemplary embodiment of the invention, device 1300 is introduced (1502) to an implantation area using fluoroscopic, CT, MRI and/or TX guidance. Using a cannula, device 1300 is passed (1504) into vertebra 1402 whereby the depressed fracture is concave in relation to the implantation area, in an embodiment of the invention. An external sheath (similar in form and function of external sheath 802) of device 1300 is removed (1506) and inner section 1302 is inflated (1508) with a biocompatible filler until the bone regains its intended shape, in an embodiment of the invention. Outer section 1304 is then inflated (1510) and internal section 1302 is deflated and optionally withdrawn (1512) from the implantation area, in an embodiment of the invention. In an embodiment of the invention, the bone whose fracture has been reduced is reinforced by filling (1514) the cavity left in external section 1304 by optional withdrawal (1512) and/or deflation of inner section 1302 with at least one biocompatible and/or biodegradable filler, for example a cement. In an exemplary embodiment of the invention, outer section 1304 is deflated (1516) and optionally removed, any implantation devices remaining in use are removed (1518) and the patient is closed (1520). Alternatively, outer section 1304 is sealed (1522) in an inflated state, for example as described herein with respect to other embodiments, and remains in place permanently or until it biodegrades.

Figure 16:
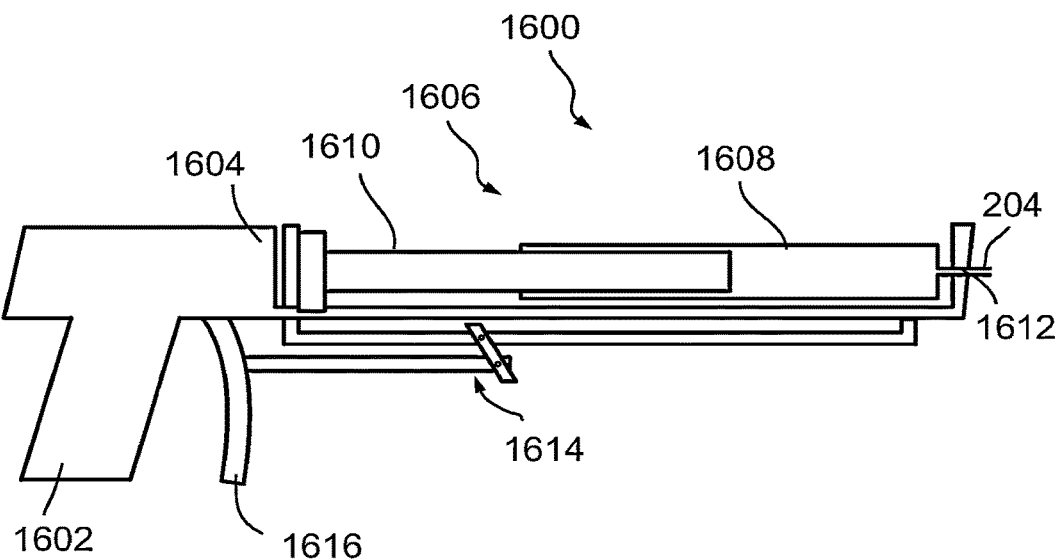
FIG. 16 is a cutaway side view of a prosthetic inflation device, in accordance with an exemplary embodiment of the invention; and, FIG. 17 is a cutaway side view of an alternate prosthetic inflation device, in accordance with an exemplary embodiment of the invention.

Referring to FIG. 16, a cutaway side view of a prosthetic inflation and/or implantation device 1600 is shown, in accordance with an exemplary embodiment of the invention. Prosthesis inflation and/or implantation device 1600 includes a grip 1602 adapted to be grasped in one hand by a medical professional performing the implantation procedure, in an embodiment of the invention. In some embodiments of the invention, device 1600 includes a housing 1604 adapted to mount therein a device inflation mechanism, for example a syringe 1606 comprising at least a canister 1608 and a plunger 1610, plunger 1610 adapted to travel within canister 1608 and expel filler out of canister 1608 via an outlet 1612 and into tube 204, described above. In an embodiment of the invention, syringe 1606 is adapted to hold and/or inject 5-20 cc of filler. It should be noted however, that syringe 1606 is adapted to hold and/or or inject more or less filler depending on the intended application of syringe 1606 and/or needs of the patient. In some embodiments of the invention, device 1600 includes a compression assembly 1614 adapted to apply force for at least for advancement of plunger 1610 in canister 1608 upon activation of a trigger 1616. Additionally and/or optionally, compression assembly 1614 is adapted to apply force for retraction of plunger 1610. In some embodiments of the invention, device 1600 is used to direct a prosthesis into an implantation site, as the prosthesis is removably connected to device 1600 via tube 204.

Figure 17:
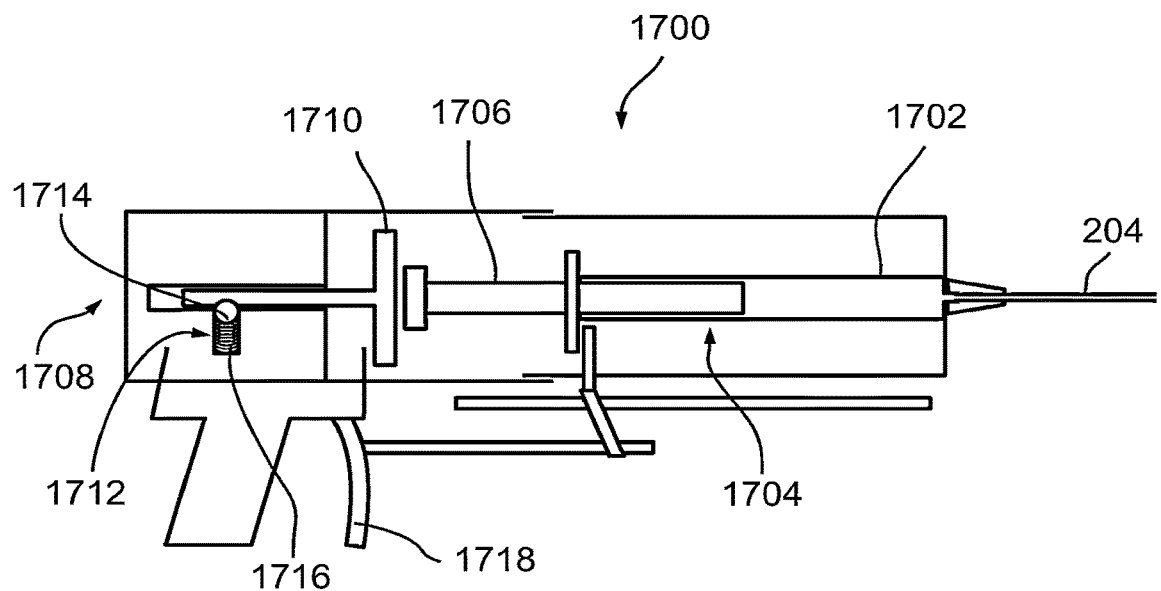

Referring to FIG. 17, a cutaway side view of an alternate prosthetic inflation and/or implantation device 1700 is shown, in accordance with an exemplary embodiment of the invention. In contrast to device 1600, which advances and/or retracts plunger 1610, device 1700 is adapted to advance and/or retract a canister 1702 portion of a syringe 1704 with a plunger 1706 portion remaining relatively fixed in relation to device 1700. Plunger 1706 portion is provided with counterforce, as canister 1702 portion is moved towards a proximal end 1708 of device 1700, by a backstop 1710, in an embodiment of the invention. Backstop 1710, in some exemplary embodiments of the invention, is fixed to device 1700. In an embodiment of the invention, the placement of the backstop is according to a predetermined level of desired inflation of the prosthesis.

In an embodiment of the invention, device 1700 is provided with a safety 1712 at least to prevent over-inflation of a prosthesis attached thereto. Safety 1712 in some embodiments of the invention, is comprised of a ball 1714 and a spring 1716 whereby ball 1714 and backstop 1710 are adapted to be counterparts such that ball 1714 releasably fits into a groove on backstop 1710 shaped to receive ball 1714. In an embodiment of the invention, once canister 1702 is advanced maximally by depressing a trigger 1718, further force on trigger 1718 will cause safety 1712 to disengage backstop 1710 as a result of ball 1714 popping out of the groove on backstop 1710 as backstop 1710 moves towards proximal end 1708 under the effect of further force. It should be noted that once safety 1712 has disengaged backstop 1710 and therefore, syringe 1704 is no longer being provided with a counterforce, continued depressing of trigger 1718 results in at least a partial retraction of tube 204 and appurtenant parts. In an embodiment of the invention, device 1700 is adapted to be used by one hand of an attending medical professional.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

What is claimed is:

1. A shoulder implant for simulating a naturally occurring bursa proximal to or in lieu of a subacromial bursa, the shoulder implant comprising:
   an expandable member expandable to at least one of a size and a shape sufficient to fill a space beneath at least one of an acromion and a coracoid process of the shoulder, wherein the expandable member is seamless and defines a cavity having an orifice, and wherein the cavity, when filled, defines a filled volume of the expandable member less than a maximal volume occupied by the expandable member; and
   a rigid ring adapted to be positioned in the orifice and remain attached to the expandable member after inflation of the expandable member, wherein the rigid ring defines a lumen;
   a plug adapted to detach from an implantation or inflation device and lodge in the lumen of the rigid ring, thereby sealing the cavity,
   wherein, when implanted, the expandable member is configured to cushion and facilitate motion between at least one of a tendon and a ligament of a rotator cuff, and a bone part in the shoulder.

2. The shoulder implant of claim 1, wherein the expandable member is inflatable with a filler to the filled volume.

3. The shoulder implant of claim 1, wherein the expandable member is expandable from a circular shape or an oval shape to a cylindrical shape or an ovoid shape, respectively, having the filled volume.

4. The shoulder implant of claim 1, further comprising an anchoring device adapted to be attached to one or more of;
   a humerus head,
   the tendon, and
   the at least one of the acromion and the coracoid process in the shoulder, thereby anchoring the shoulder implant in place.

5. The shoulder implant of claim 1, wherein the expandable member having the filled volume is configured to contour to an outer surface of surrounding tissues, such that the surrounding tissues are placed within contours thereof, thereby anchoring the expandable member in place.

6. The shoulder implant of claim 1, further comprising a filler, wherein the filler comprises saline, Hartman solution, Ringer solution, gel, gas, pharmaceutical agent, and a biodegradable fluid, or any combination thereof.

7. The shoulder implant of claim 1, wherein the filled volume is about 70% or less than the maximal volume.

8. The shoulder implant of claim 1, wherein the expandable member is made of a biodegradable material.

9. The shoulder implant of claim 8, wherein the biodegradable material comprises at least one of polycaprolactone, polyglycolide, polyhydroxybutyrate, plastarch material, polyetheretherketone, zein, polylactic acid, polydioxanone, poly(lactic-co-glycolic acid), collagen, and methyl cellulose.

10. The shoulder implant of claim 1, wherein the filled volume of the expandable member is at least one of a size and a shape configured to resemble the naturally occurring bursa.

11. The shoulder implant of claim 1, wherein the expandable member having the filled volume is configured to reduce rubbing of soft tissues against other tissues of at least one of a humerus, the acromion or the coracoid process of the shoulder while permitting at least some movement of soft tissues relative to humerus, the acromion, or the coracoid process.

12. The shoulder implant of claim 11, wherein the space is determined such that the expandable member having the filled volume avoids interposition of soft tissues between the expandable member and the acromion or the coracoid process, and the expandable member remains below the acromion during movement of the humerus.

13. The shoulder implant of claim 1, wherein the expandable member is a balloon-like structure made from at least one of a biocompatible and a biodegradable synthetic material.

14. The shoulder implant of claim 1, wherein the plug is adapted to deform in the lumen.

15. The shoulder implant of claim 14, wherein a diameter of the plug exceeds an inner diameter of the lumen.

16. The shoulder implant of claim 14, wherein the plug is formed of a biodegradable material.

17. An implant system comprising:
    the shoulder implant of claim 14; and
    the implantation or inflation device, wherein the implantation or inflation device is detachably attached to the plug at a first end of the implantation or inflation device.

18. The implant system of claim 17, wherein the lumen provides fluid communication between the implantation or inflation device and the cavity.

19. The implant system of claim 17, wherein the implantation or inflation device defines an opening adapted to allow passage of a filler through the implantation or inflation device into the cavity.

20. The implant system of claim 17, wherein the implantation or inflation device extends through the lumen such that the plug and the first end of the implantation or inflation device are disposed inside the cavity.

21. The implant system of claim 20, wherein the implantation or inflation device slidably extends through the lumen.

22. The implant system of claim 21, wherein the implantation or inflation device is configured such that slidably removing the first end of implantation or inflation device from the cavity through the lumen lodges the plug in the lumen, thereby sealing the cavity.

23. The implant system of claim 22, wherein a diameter of the plug exceeds an inner diameter of the lumen.

24. The implant system of claim 17, further comprising a cannula, wherein the expandable member is positioned in the cannula.

25. The implant system of claim 24, wherein the expandable member is adapted to be inserted into a patient's body through the cannula.

* * * * *